United States Patent [19]

Fukukita et al.

[11] Patent Number: 4,817,615

[45] Date of Patent: Apr. 4, 1989

[54] ULTRASONIC TEMPERATURE MEASUREMENT APPARATUS

[75] Inventors: Hiroshi Fukukita; Shinichiro Ueno, both of Tokyo; Masayuki Tone; Tsutomu Yano, both of Kawasaki, all of Japan

[73] Assignee: Matsushita Electric Industrial Co., Ltd., Japan

[21] Appl. No.: 941,221

[22] Filed: Dec. 12, 1986

[30] Foreign Application Priority Data

Dec. 13, 1985 [JP] Japan .................................. 60-281336
Mar. 28, 1986 [JP] Japan .................................. 61-71537
Mar. 28, 1986 [JP] Japan .................................. 61-71538
Mar. 28, 1986 [JP] Japan .................................. 61-71539
Mar. 28, 1986 [JP] Japan .................................. 61-71540
Mar. 28, 1986 [JP] Japan .................................. 61-71542

[51] Int. Cl.$^4$ ............................................. A61B 10/00
[52] U.S. Cl. ............................................. 128/660.02
[58] Field of Search .................... 128/660, 24 A, 736, 128/660; 73/861.01

[56] References Cited

U.S. PATENT DOCUMENTS

| | | | |
|---|---|---|---|
| 3,771,116 | 11/1973 | Farrah | 367/8 |
| 3,771,355 | 11/1973 | Sachs | 356/419 |
| 4,322,974 | 4/1982 | Abele et al. | 73/602 |
| 4,620,546 | 11/1986 | Aida et al. | 128/660 |
| 4,664,124 | 5/1987 | Ingle et al. | 128/660 |

FOREIGN PATENT DOCUMENTS 0152113 8/1985 European Pat. Off. .
59-226841 12/1984 Japan .
8401432 4/1984 PCT Int'l Appl. .
8401890 5/1984 PCT Int'l Appl. .

OTHER PUBLICATIONS

Journal of the Acoustical Society of America, vol. 69, No. 6, Jun. 1981, pp. 1834–1840, Acoust. Soc. Am., New York, US; Y. Hayakawa et al.: "Multifrequency Echoscopy for Quantitative Acoustical Characterization of Living Tissues".

Journal of the Acoustical Society of America, vol. 45, No. 5, May 1969, pp. 1251–1257, New York, US; R. C. Williamson: "Echo Phase-Comparison Technique and Measurement of Sound Velocity in Water".

Primary Examiner—Francis Jaworski
Assistant Examiner—George Manuel
Attorney, Agent, or Firm—Lowe, Price, LeBlanc, Becker & Shur

[57] ABSTRACT

An ultrasonic diagnostic apparatus detects variations of an acoustic characteristic to obtain the fluctuation of temperature within a body to be examined. The ultrasonic diagnostic apparatus includes an ultrasonic transducer for transmitting an ultrasonic wave and receiving the reflected ultrasonic wave which is in turn converted into an electric signal. The signal is phase-detected in accordance with a plurality of gate intervals or a plurality of window interval to detect a phase difference therebetween. The relative variation of velocity dispersion before and after heating of the body is obtained on the basis of the phase variation resulting from the variation of the ultrasonic drive frequency.

8 Claims, 11 Drawing Sheets

ULTRASONIC TEMPERATURE MEASUREMENT APPARATUS

BACKGROUND OF THE INVENTION

The present invention relates generally to an ultrasonic measuring apparatus, and more particularly to an ultrasonic diagnostic apparatus for detecting variations of an acoustic characteristic to obtain the fluctuation of temperature within a body to be examined.

The need to measure a temperature within the body of a patient is currently known, for example, in thermotherapy for cancer. Various acoustic characteristics of the tissue within the body depends upon temperature and are extremely important measuring items in diagnostics. A method of measuring the fluctuation of temperature within the body using the fact where acoustic velocity being one of the acoustic characteristics depends upon temperature is disclosed as intersection beam method in "The 45 Issue of Lecture Paper of Study Meeting of Ultrasonic Medical Society (pages 21 to 22) published in 1984.

However, such a method does not produce satisfactory results for meeting requirements in terms of accurately measuring the fluctuation of temperature even if the acoustic velocity varies depending on tissues of the body.

SUMMARY OF THE INVENTION

The present invention has been developed in order to eliminate the above-mentioned drawbacks inherent to the prior temperature measuring method.

It is therefore an object of the present invention to provide a new and improved ultrasonic diagnostic apparatus which is capable of accurately measuring the fluctuation of temperature within the body of a patient irrespective of the variations of acoustic velocity resulting from different tissues.

Another object of the present invention is to provide an ultrasonic diagnostic apparatus which is capable of obtaining data in terms of the acoustic velocity at a given portion even if the acoustic velocity varies depending upon tissues as in an organism.

A further object of the present invention is to provide an ultrasonic diagnostic apparatus which is capable of precisely obtaining the frequency dependency of acoustic phase velocity on a given tissue within an organism.

According to a feature of the present invention, ultrasonic echo signal is phase-detected in accordance with a plurality of gate intervals or a plurality of window intervals to detect the phase difference, and the relative variation of velocity dispersion shown before and after heating of a body to be examined is obtained on the basis of the phase variation resulting from the variation of ultrasonic drive frequency.

According to a further feature of the present invention, ultrasonic pulses with different frequencies are transmitted into a body to be examined, and then received signals are phase-detected in accordance with a plurality of gate intervals to obtain phase differences in each gate interval, and the variations of the phase differences caused by varying the conditions of the ultrasonic pulses is measured.

In accordance with an embodiment of the present invention, there is provided an ultrasonic measuring apparatus comprising: ultrasonic transducer means driven in response to a plurality of frequencies for receiving ultasonic waves reflected from a body to be examined and for converting the reflected ultrasonic waves into electric signals; phase detecting means for phase-detecting the signal from said ultrasonic transducer means in synchronism with the frequencies; timing generator means for generating a plurality of gate intervals in synchronism with the driving of said ultrasonic transducer means; and computing means for obtaining phase differences at the plurality of gate intervals as for the plurality of frequencies in accordance with the output of said phase detecting means and for computing a dispersion, which is a variation component of the phase difference between the frequencies, and the relative variation between the dispersion.

In accordance with a further embodiment of the present invention, there is provided an ultrasonic measuring apparatus comprising: ultrasonic transducer means for receiving an ultrasonic wave reflected from a body to be examined and for converting the reflected ultrasonic wave into an electric signal; amplifier means for amplifying the signal from said ultrasonic transducer means; discrete Fourier transformaion means for performing a discrete Fourier transformation in terms of the output of said amplifier with a plurality of window intervals; phase difference computing means for obtaining a phase difference of the output data from said discrete Fourier transformation means in accordance with the plurality of window intervals; frequency change rate computing means for obtaining the rate of change of frequency in terms of the output data from said phase difference computing means; and temperature change rate computing means for obtaining the rate of change of temperature on the basis of the obtained rate of change of frequency.

In accordance with a further embodiment of the present invention, there is provided an ultrasonic measuring apparatus comprising means for generating a plurality of drive pulses whose frequencies are different from each other; timing control means for controlling phases between the plurality of drive pulses; ultrasonic transducer means coupled to said drive pulse generating means; phase detecting means for performing a phase detection in terms of signals from said ultrasonic transducer means; means for changing the detection frequency of said phase detecting means; gate interval generating means for generating a plurality of gate intervals in synchronism with said drive pulse generating means; phase difference computing means for obtaining a phase difference in terms of the outputs of said phase detecting means in accordance with the gate intervals; and phase shift computing means for obtaining the difference between the outputs of the phase difference computing means corresponding to the different conditions of said timing control means or corresponding to different detection frequencies.

In accordance with a further embodiment of the present invention, there is provided an ultrasonic measuring apparatus comprising: ultrasonic vibrator means for transmitting and receiving an ultrasonic wave; transmission timing generating means for generating a transmission timing signal; transmission pulse means for generating a transmission pulse in synchronism with said transmission timing signal; gate pulse generating means for generating a gate pulse in synchronism with said transmission timing signal; switching timing means for generating a switching timing control signal on the basis of said gate pulse; transmission pulse switching means provided between said ultrasonic vibrator means and transmission pulse means for switching the transmission pulse from said transmission pulse means on the basis of the switching timing control signal; variable frequency generator means coupled to said transmission pulse means; amplifier means for amplifying the signal corresponding to the wave received by said ultrasonic vibrator; phase detection signal generating means for generating a phase detection signal in synchronism with a clock from said variable frequency generator means; first and second phase detectors for quadrature-phase-detecting the output of said amplifier means in accordance with the phase detection signal; first and second integrators for integrating the outputs of said first and second phase detectors within interval of the gate pulse produced in synchronism with the transmission timing signal; first and second A/D converters for converting the outputs of said first and second integrators into digital values; first and second memory sections for receiving the output value of said first A/D converter through first memory switching means controlled in accordance with the switching timing control signal; first subtraction means for calculating the difference between the outputs of said first and second memory sections; third and fourth memory sections for receiving the output value of said second A/D converter through second memory switching means controlled in accordance with the switching timing control signal; second subtraction means for calculating the difference between the outputs of said third and fourth memories; and computing means for obtaining a phase on the basis of output value of said first and second subtraction means.

BRIEF DESCRIPTION OF THE DRAWINGS

The object and features of the present invention will become more readily apparent from the following detailed description of the preferred embodiments taken in conjunction with the accompanying drawings in which.

DETAILED DESCRIPTION OF THE INVENTION

Figure 1:
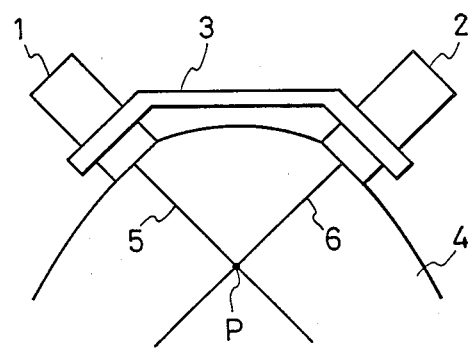
FIG. 1 is a diagram showing a conventional ultrasonic measuring apparatus.

Prior to describing embodiments of the present invention, a brief description of the above-mentioned prior intersection beam method will be first made with reference to FIG. 1 for the purpose of assisting in the understanding of the invention.

The prior intersection beam system, as shown in the figure, comprises a pair of ultrasonic transducers 1, 2 for transmitting and receiving an ultrasonic wave, a holding device 3 for holding the ultrasonic transducers 1, 2 with predetermined angle and space. Numerals 5 and 6 respectively represent the directions of a beam from the ultrasonic transducer 1 into a body 4 to be examined and a beam from the ultrasonic transducer 2 thereinto. The beams from the pair of ultrasonic transducers 1, 2 intersect each other at a point P within the body 4.

The ultrasonic transducer 1 transmits an ultrasonic pulse signal into the body 4 in response to a drive pulse signal. The transmitted ultrasonic pulse signal advances in the beam direction 5 while being scattered by the tissues of the body 4, and thereafter reaches the point P. A portion of the ultrasonic pulse signal scattered thereby propagates in the direction reverse to the beam direction 6 and reaches the ultrasonic transducer 2. Since the propagation distance along the beam directions 5 and 6 depends upon the geometrical distance between the ultrasonic transducers 1, 2 passing through the point P, measuring the propagation time of the ultrasonic pulse allows obtaining the acoustic velocity within the body 4.

However, according to the above-described arrangement, it is rendered possible to measure the acoustic velocity under the condition that the acoustic velocity is constant at any places of the tissues within an organism. In cases where the acoustic velocity varies depending upon tissues as in an actual organism, the acoustic beam is refracted in a complicated manner, providing large errors if the acoustic velocity is obtained in accordance with linear approximation. This results in inefficiency because the variation of the acoustic velocity caused by heating is as small as about 1% and it is required to precisely perform the measurement of acoustic velocity. Furthermore, it is impossible according to the above-mentioned arrangement to accurately obtain the fluctuation of temperature based on partial increase in temperature.

Figure 2:
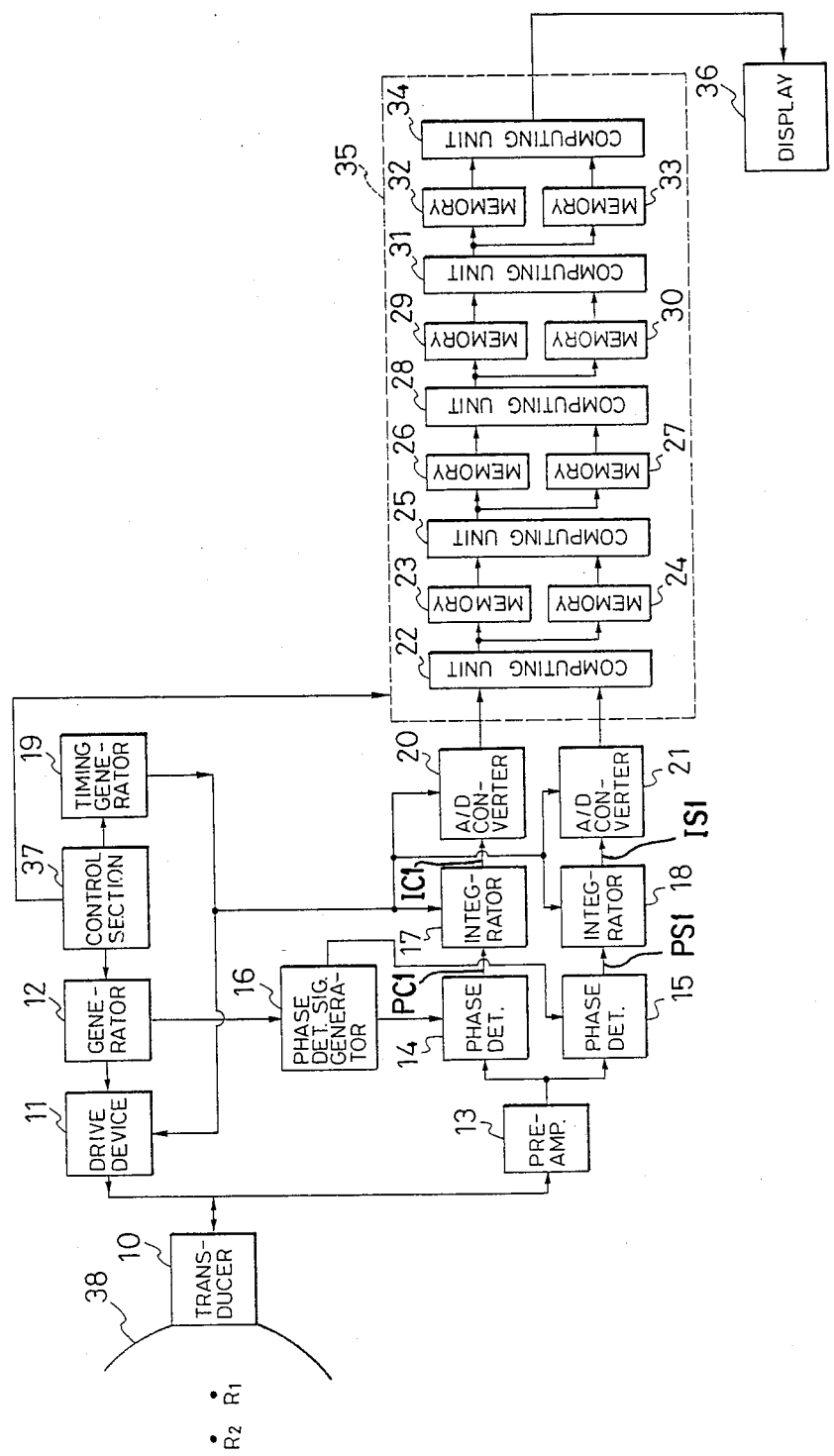
FIG. 2 is a block diagram showing an ultrasonic measuring apparatus according to a first embodiment of the present invention.

Referring now to FIG. 2, there is illustrated an ultrasonic diagnostic apparatus according to an embodiment of the present invention.

In FIG. 2, the reference numeral 10 represents an ultrasonic transducer, numeral 11 designates a pulse drive device for driving the ultrasonic transducer 10, numeral 12 depicts a variable frequency generator for supplying a clock signal CK1 to the pulse drive device 11, numeral 13 is a preamplifier for amlifying a received signal from the ultrasonic transducer 10, numerals 14 and 15 are phase detectors coupled to the output of the preamplifier 13, numeral 16 is a phase detecting signal generator for supplying the phase detectors 14, 15 with quadrature phase detecting signals COS and SIN in synchronism with a clock signal CK2 from the variable frequency generator 12. The numerals 17 and 18 are integrators for integrating the outputs of the phase detectors 14 and 15, numeral 19 represents a timing generator for supplying a gate pulse signal g to the integrators 17, 18 and for supplying transmission timing signal TX and so on to the pulse drive device 11, numerals 20 and 21 are A/D converters for converting the outputs of the integrators 17, 18 into digital signals, numeral 22 designates a computing unit for computing a phase angle of the outputs of the A/D converters 20, 21. Numerals 23, 24 are memories for storing phase angle data between adjacent gate pulses, numeral 25 is a computing unit for deriving phase difference data from the data in the memories 23, 24, numerals 26, 27 are memories for storing phase difference data in terms of frequencies before and after the generated frequency of the variable frequency generator 12 is varied, numeral 28 represents a computing unit for computing dispersion data from the data in the memories 26, 27, numerals 29, 30 are memories for storing a distribution data obtained on the basis of the different frequencies from the variable frequency generator 12, and numeral 31 is a computing unit for computing speed ratio data from the data in the memories 29, 30. Numerals 32, 33 are memories for storing speed ratio data before and after variation on an examined body such as increase in temperature, numeral 34 is a computing unit for obtaining a relative variation of the speed ratio data from the data in the memories 32, 33. A computing section 35 comprises computing units 22, 25, 28, 31 and 34. Furthermore, numeral 36 represents a display section for displaying the output of the computing device 34 and so on, numeral 37 is a control section for controlling the variable frequency generator 12, timing generator 19, computing section 35 and so on, and numeral 38 represents a body to be examined which includes reflectors R1 and R2.

A description of the operation of the above-mentioned arrangement will be made hereinbelow.

When driven in response to a pulse with an angular frequency $\omega$ from the pulse drive device 11, the ultrasonic transducer 10 transmits an ultrasonic pulse signal into the body 38 to be examined. The ultrasonic pulse is reflected successively at the reflectors R1 and R2 and received by the ultrasonic transducer 10 to produce received signals, which are respectively expressed with the references e1 and e2. The change in pulse spacing between the received signals e1 and e2 can be obtained in accordance with the phase detection technique. Alternating current components S1 and S2 of the received signals e1 and e2 are expressed by the following equations.

$$S1 = \cos(\omega t + \phi)$$
$$S2 = \cos\{\omega(t - \Delta t) + \phi\} \quad (1)$$

where $\phi$ is constant.

$\Delta t$ is a time taken for going and returning in terms of a distance $\Delta x$ between the reflectors R1 and R2, and therefore $\Delta t$ can be expressed as follows.

$$\Delta t = 2\Delta x / Co(\omega 8A.B) \quad (2)$$

where $C(\omega)$ is an acoustic phase velocity between the reflectors R1 and R2 within the examined body 38 and is expressed as a function of the angular frequency $\omega$ for obviously indicating the dispersion. The alternating current components S1 and S2 are quadrature-phase-detected with the angular frequency $\omega$ in the phase detectors 14 and 15. The phase detection outputs PC1 and PS1 of the alternating current component S1 corresponding to the reflector R1 are expressed in accordance with the following equations.

$$PC1 = \cos(\omega t + \phi) \times \cos\omega t$$
$$PS1 = \cos(\omega t + \phi) \times \sin\omega t \quad (3)$$

The phase detection outputs PC1 and PS1 are respectively integrated in the integrators 17 and 18. The integration is performed at a first gate interval produced by the timing generator 19. The outputs IC1 and IS1 of the integrators 17, 18 corresponded to the values obtained by removing high frequency components from the phase detection outputs PC1 and PS1 of the equation (3), and therefore can be expressed as follows.

$$IC1 = \cos\phi$$
$$IS1 = \sin\phi \quad (4)$$

The outputs IC1 and IS1 of the integrators 17, 18 are converted by the A/D converters 20, 21 into the digital signals, and a phase $\phi1$ is calculated as follows.

$$\phi1 = \tan^{-1}(IS1/IC1) = \phi \quad (5)$$

Similarly, the alternating current component S2 of the received signal e2 due to the reflector R2 is phase-detected by the phase detectors 14 and 15 and then integrated at a second gate interval produced by the timing generator 19. The outputs IC2 and IS2 of the integrators and phase $\phi2$ are respectively expressed in accordance with the following equations.

$$IC2 = \cos(-\omega \cdot \Delta t + \phi)$$
$$IS2 = \sin(-\omega \cdot \Delta t + \phi) \quad (6)$$
$$\phi2 = \tan^{-1}(IS2/IC2) = -\omega \cdot \Delta t + \phi \quad (7)$$

The phases $\phi1$ and $\phi2$ are respectively stored in the memories 23 and 24. The difference between the phases $\phi1$ and $\phi2$, i.e., phase difference $\Delta\phi$ can be obtained as follows in accordance with the subtraction performed by the computing unit 25.

$$\Delta\phi = \phi1 - \phi2 = \omega \cdot \Delta t = \omega \cdot \frac{2\Delta x}{C(\omega)} \quad (8)$$

The process for obtaining phase difference $\Delta\phi$ described above is performed with respect to the adjacent angular frequencies $\omega1$ and $\omega2$, respectively. The change of the angular frequency is effected by specifying the generating frequency of the variable frequency generator 12. The angular frequency $\omega2$ is expressed by $\omega1 + \Delta\omega$. The phase difference $\Delta\phi1$ with respect to the angular frequency $\omega1$ and the phase difference $\Delta\phi2$ with respect to the angular frequency $\omega2$ are respectively stored in the memories 26 and 27. Dispersion data $\Delta\Delta\phi$, which is the difference between the phase differences $\Delta\phi1$ and $\Delta\phi2$ are obtained as follows by subtraction in the computing unit 28.

$$\Delta\Delta\phi = \Delta\phi1 - \Delta\phi2 \quad (9)$$
$$= \omega1 \frac{2\Delta x}{Co(\omega1)} - (\omega1 + \Delta\omega) \frac{2\Delta x}{Co(\omega1 + \Delta\omega)}$$

Assuming that $\Delta\omega$ in the equation (9) is small and it is possible to disregard the variation of the acoustic velocity $Co(\omega)$ resulting from the variation of the angular frequency ω, the dispersion data is expressed by the following equation.

$$\Delta\Delta\phi = \frac{\Delta\omega \cdot 2\Delta x}{Co(\omega 1)} \quad (10)$$

Hereinafter, the dispersion data in terms of the angular frequency ω1 will be expressed by $\Delta\Delta\phi 1$ and the distributed data in terms of the angular frequency $\omega n = \omega 1 + (n-1)\Delta\omega$ will be expressed by $\Delta\Delta\phi n$. The dispersion data $\Delta\Delta\phi 1$ and $\Delta\Delta\phi n$ are stored in the memories 29 and 30, respectively. The velocity ratio data $R\phi$ with respect $\Delta\Delta\phi 1$ and $\Delta\Delta\phi n$ is obtained as follows by division in the computing unit 31.

$$R\phi = \frac{\Delta\Delta\phi n}{\Delta\Delta\phi 1} = \frac{Co(\omega 1)}{Co(\omega 2)} \quad (11)$$

As expressed by the equation (11), the velocity ratio data $R\phi$ is varied relative to the velocity $Co(\omega)$, and does not depend upon the distance $\Delta x$ between the reflectors R1 and R2. Therefore, it is an efficient value irrespective of the variation of the distance $\Delta x$ after heating. The relative variation $\Delta R\phi$ of the velocity ratio data $R\phi$ can be calculated in the computing unit 34 by storing the varying state of the velocity ratio data $R\phi$ obtained before and after heating in the memories 32 and 33. For example, it is appropriate that the relative variation $\Delta R\phi$ is obtained by normalizing the variation component of the speed ratio data $R\phi$ after heating on the basis of the speed ratio data $R\phi$ before heating. The relative variation $\Delta R\phi$ is displayed by numeric on the display section 36.

As typical examples in terms of dispersion of the acoustic velocity $Co(\omega)$, under the condition that the frequency is between 1 to 2 MHz, the variation of velocity of a lever is about 1.5 m/sec and the variation of velocity of a muscle is about 3 m/sec. It is understood that the temperature dependence is smaller, and therefore the sufficient accuracy is required for calculation of the velocity ratio data $R\phi$ in the equation (11). In order to reduce error in digital calculation, it is proper to measure the velocity ratio data $R\phi$ many times and to average the results of the measurements in the computing unit 34 after all the results are stored in the memories 32 and 33. Furthermore, it is appropriate to use the average value of the velocity ratio data $R\phi$ in a plurality of portions of the examined body which are obtained by slightly scanning the ultrasonic transducer 10. It is considered that the ultrasonic beam pattern of the ultrasonic transducer 10 affects the measurement of the acoustic velocity. In order to avoid the affection, it may be desired to obtain the average value of the velocity ratio $R\phi$ obtained shifting the ultrasonic transduced 10 slightly in the beam advancing direction. In addition, it is also appropriate to obtain the average value of the velocity ratio data $R\phi$ obtained by shifting the position of electronic focus formed by an array of ultrasonic transducers coupled to a plurality of RF pulse drive devices.

The above disclosure has been described in terms of two independent reflectors within the body 38. It is considered in actual organism that reflection echoes from plurality of scatterers are superimposed at the time width corresponding to the gate interval for integration. However, the above description be also applicable to this case.

In order to make clear the measurement positions within an organism, the gate interval for integration may be displayed on an ultrasonic tomographic image. In displaying the gate interval, it is appropriate to display a gray scale or color code positioned corresponding to the relative variation $\Delta R\phi$.

Figure 3:
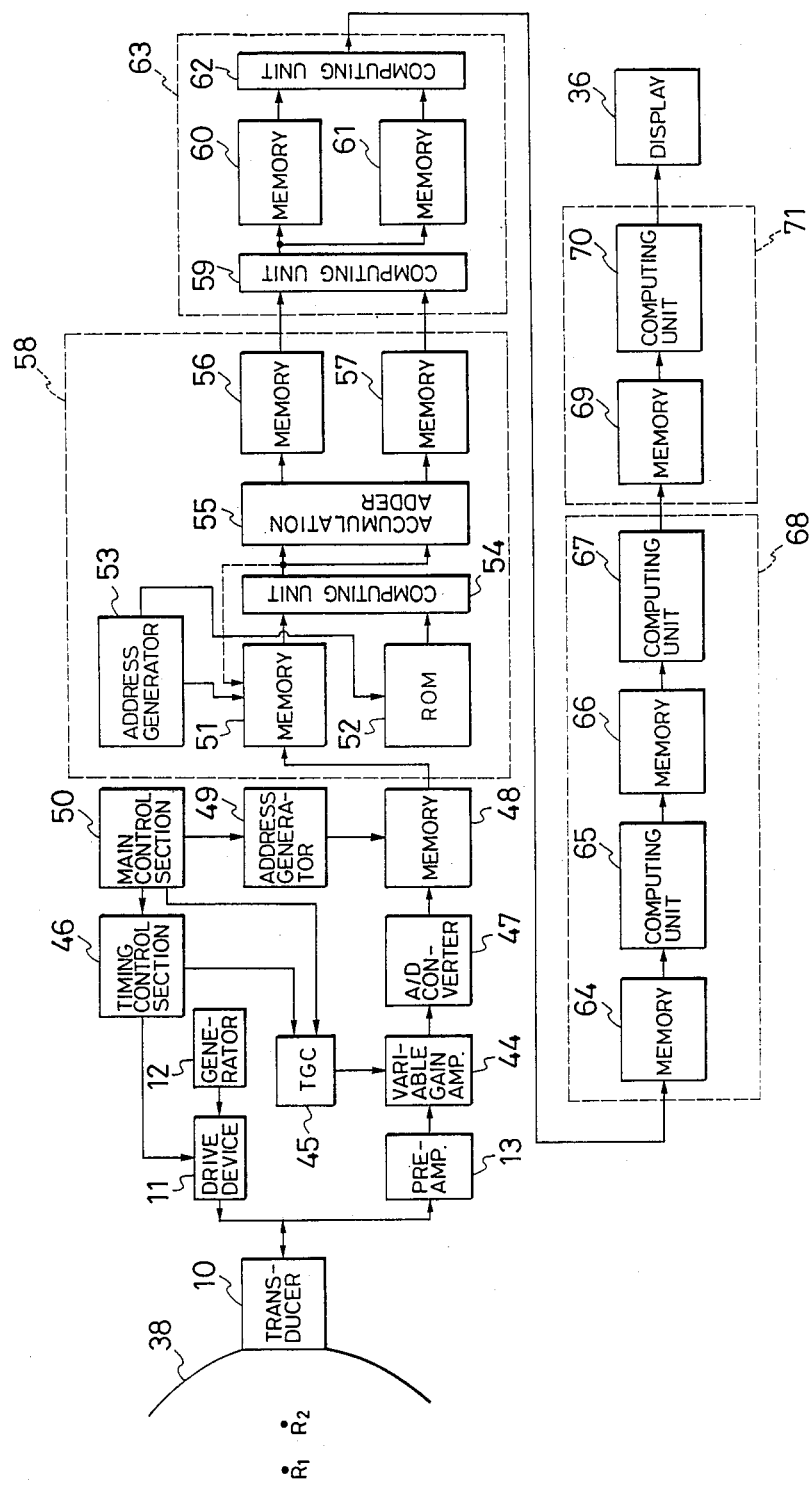
FIG. 3 is a block diagram showing an ultrasonic measuring apparatus according to second embodiment of the present invention.

FIG. 3 is a block diagram showing an ultrasonic diagnostic apparatus according to a second embodiment of the present invention.

In FIG. 3, numeral 10 represents an ultrasonic transducer, numeral 11 designates a pulse drive device for driving the ultrasonic transducer 10, numeral 12 depicts a generator for determining the RF frequency of the RF pulse from the pulse drive device 11. Numeral 13 is a preamplifier for amplifying a signal received by the ultrasonic transducer 10, numeral 44 is a variable gain amplifier for amplifying the output of the preamplifier 13, numeral 45 represents a time gain compensator (which will be hereinafter referred to as TGC) for controlling the gain of the variable gain amplifier 44 in accordance with time. Numeral 46 is a timing control section for controlling the operating timings of the pulse drive device 11 and the TGC 45, numeral 47 is an A/D converter for converting the output of the variable gain amplifier 44 into digital data, numeral 48 designates a memory for storing the output of the A/D converter 47, and numeral 49 is an address generator for producing the address of the memory 48. Numeral 50 represents a main control section for controlling the whole system including the timing control section 46, TGC 45, address generator 49 and so on, numeral 51 is a memory for storing data corresponding to a specific window interval of the data stored in the memory 48, numeral 52 designates a read-only memory (which will be hereinafter referred to as ROM) for storing constants necessary for performing discrete Fourier transformation, numeral 53 is an address generator for producing addresses of the memory 51 and ROM 52, numeral 54 is a multiplication unit for performing the multiplication of the data outputted from the memory 51 and ROM 52 and for restoring the result to the memory 51 or supplying the same to an accumulation adder 55 in the next stage. The accumulation adder 55 performs accumulating addition in terms of the output of the multiplication unit 54. Whenever the angular frequency of the discrete Fourier transformation is varied, the output of accumulation adder 55 is written in a memories 56 and 57. The real part of the discrete Fourier transformation is written in the memory 56 and the imaginary part thereof is written in the memory 57. A discreate Fourier transformation section comprises the memory 51, ROM 52, address generator 53, multiplication unit 54, accumulation adder 55, and memories 56, 57.

Numeral 59 represents a computing unit for computing a arrangement $\phi$ of a complex number when the data of the memory 56 is the real part and the data of memory 57 is imaginary part, numeral 60 is a memory for storing a argument $\phi$ corresponding to a specific window interval, numeral 61 designates a memory for storing an argument corresponding to a window interval different from the specific window interval, numeral 62 depicts a computing unit for obtaining the phase difference $\Delta\phi$ between the different window intervals by calculating the difference between arguments $\phi$ stored in the memories 30 and 31. A phase difference computing section 63 comprises the memories 60, 61 and computing units 59, 62.

Numeral 64 designates a memory for storing the phase difference $\Delta\phi$, numeral 65 is a computing unit for computing dispersion data $\Delta\Delta\phi$ on the basis of the phase difference $\Delta\phi$ stored in the memory 64, numeral 66 is a memory for storing dispersion data $\Delta\Delta\phi$, numeral 67 represents a computing unit for calculating the rate of change of frequency $R\phi$ on the basis of dispersion data $\Delta\Delta\phi$ stored in the memory 66. A change rate computing section 68 comprises the memories 64, 66 and computing units 65 and 67. Numeral 69 is a memory for storing the speed ratio data $R\phi$, numeral 70 represents a computing unit for computing the rate of change of temperature on the basis of the speed ratio data stored in the memory 69. A temperature change rate computing section comprises the memory 69 and the computing unit 70. Numeral 36 is a display section for displaying the rate of change of temperature and numeral 38 is a body to be examined.

A description of operation of the above-mentioned arrangement will be made hereinbelow.

First of all, when driven by the pulse drive device 11, the ultrasonic transducer 10 transmits an ultrasonic pulse into a body 38 to be examined. The ultrasonic pulse is sequentially reflected by reflectors R1 and R2 within the body 38 and the reflected pulses are converted by the ultrasonic transducer 10 into received signal. The waveforms of the received signals are expressed with h1 and h2. The following description is made in terms of how the phases of h1 and h2 are varied.

As in the case of organism tissues, when the attenuation of ultrasonic wave is increased in proportion to the first power of the frequency, it is disclosed in "ULTRASONIC IMAGING (Vol. 4, 1982, pages 355 to 377)" that the relation expressed by the following equation (12) is satisfied.

$$\frac{1}{Co(\omega)} = \tau - \frac{\beta}{\pi^2} \ln(\omega) \qquad (12)$$

where: $\omega$ is angular frequency; $V(\omega)$ is phase velocity; $\tau$ is delay time; $\beta$ is slope of frequency dependent attenuation.

It is understood from the equation (12) that the phase velocity $V(\omega)$ depends upon frequency, that is, distribution is effected. The phase velocity difference $\Delta Co$ in terms of the angular frequencies $\omega 1$ and $\omega 2$ can be expressed as follows.

$$\Delta Co = Co(\omega 2) - Co(\omega 1) \qquad (13)$$
$$= \frac{\beta}{\pi^2} \ln\left(\frac{\omega 2}{\omega 2}\right) \cdot V(\omega 1) \cdot V(\omega 2)$$

If $\omega 2/\omega 1 = 2$, $\Delta Co$ in fat tissue is about 1 m/sec and $\Delta V$ in muscle is about 3 m/sec. Furthermore, it is also understood that since the frequency gradient $\beta$ depends upon temperature, $\Delta V$ also depends upon temperature.

On the other hand, the phase difference $\Delta\phi$ in terms of the angular frequencies $\omega$ of the received signal waveforms h1 and h2 is expressed in accordance with the following equation.

$$\Delta\phi = \frac{2 \cdot \Delta x}{C(\omega)} \qquad (14)$$

where $\Delta x$ is a distance between the reflectors R1 and R2, which is unknown amount because it exists within the body to be examined.

The dispersion ratio data $\Delta\Delta$, which is the variation of the phase differences $\Delta\phi$ when the frequency $\omega$ is varied by $\Delta\omega$, can be approximated in accordance with the following equation as the variation of the phase velocity $V(\omega)$ is small.

$$\Delta\Delta\phi(\omega 1) = \frac{2 \cdot \Delta x}{V(\omega 1)} \cdot \omega 1 - \frac{2 \cdot \Delta x}{V(\omega 1 + \Delta\omega)} \cdot (\omega 1 + \Delta\omega) \qquad (15)$$
$$\simeq \frac{2 \cdot \Delta x}{C(\omega 1)} \cdot \Delta\omega$$

The velocity ratio data $R\phi$, which is the ratio of dispersion data $\Delta\Delta\phi$ when the angular frequency $\omega$ is greatly varied from $\omega 1$ to $\omega 2$, is expressed as follows.

$$R\phi = \frac{\Delta\Delta\phi(\omega 1)}{\Delta\Delta\phi(\omega 2)} = \frac{C(\omega 2)}{V(\omega 1)} = 1 + \frac{\Delta V}{V(\omega 1)} \qquad (16)$$

Accordingly, it is ratio of the phase velocities. In the equation (16), it is important that the distance $\Delta x$, which is the unknown amount, is eliminated.

As the above, by performing analysis and process in terms of the waveforms h1 and h2 of the received signals, it is understood that the velocity ratio data $R\phi$ of the phase velocity in terms of the angular frequencies $\omega 1$ and $\omega 2$ can be obtained. $(R\phi - 1)$ is expressed as follows using the equations (16) and (13).

$$(R\phi - 1) = \frac{\Delta V}{V(\omega 1)} = \frac{\beta}{\pi^2} \ln\left(\frac{\omega 2}{\omega 1}\right) \cdot V(\omega 2) \qquad (17)$$

$(R\phi - 1)$ is proportional to the slope of frequency dependent attenuation $\beta$ that is, it depends upon temperature. Whereupon, when the value of $(R\phi - 1)$ is recorded before and after heating of the body 38 to be examined, it is possible to estimate the increase in temperature within the body caused by the heating on the basis of the temperature dependence data of $\beta$. Furthermore, the value of $(R\phi - 1)$ can be obtained irrespective of the distance $\Delta x$ between the reflectors R1 and R2. This provides an advantage in that it is not affected by the variation of the distance $\Delta x$ after heating for a long time.

Secondly, a description is made in terms of how the value of $(R\phi - 1)$ is obtained in FIG. 3.

The received signal from the ultrasonic transducer 10 is amplified in the preamplifier 13 and further amplified in the variable gain amplifier 14 under control of the TGC 15. The TGC 15 controls the gain of the variable gain amplifier 14 so as to compensate for the attenuation of the ultrasonic pulse within the body 38 to be examined. The output of the variable gain amplifier 14 is converted by the A/D converter 47 into digital sample data spring X(n), where n=1 to N. It is desired that the A/D converter 47 has great number of bits and the sampling operation is performed a high speed corresponding to more than ten times ultrasonic frequency. After sampling data series X(n) is stored in the memory 48, the data series H(1) to H(M) corresponding to the received signal waveform h1 is transmitted to the memory 21. The discrete Fourier transformation is performed in terms of the data series H(1) to H(M) in accordance with the formula indicated by an equation (18).

$$Z(\omega i) = \sum_{m=1}^{M} H(m) \cdot \exp(j \cdot \omega i \cdot \Delta T \cdot m) \qquad (18)$$

$$Z(\omega i) = R(\omega i) + jX(\omega i)$$

where $\Delta T$ is sampling time interval.

The constant $\exp(j \cdot \omega i \cdot \Delta T \cdot m)$ of the multiplication in the equation (18) is stored in the ROM 52. The multiplication of $H(m)$ and the constant is performed in the multiplication unit 54 and the accumulation $\Sigma$ is effected by the accumulation adder 55. The real part $R(\omega i)$ in the result of the discrete Fourier transformation is stored in the memory 56 and the imaginary part $X(\omega i)$ therein is stored in the memory 57. It is proper that the weight constant of the window interval is further stored in the ROM 52. It is well known with respect to the result obtained in the case of performing the discrete Fourier transformation in terms of the data string which the weight constant is multiplied. The selection of the data string $H(m)$ from the sample data series $X(n)$ is performed in accordance with the setting of the window interval by the main control section 56 and the corresponding address generation by the address generator 49. Similarly, the data series corresponding to the received signal waveform h2 results in the discrete Fourier transformation and then stored in the memories 56 and 57. the phase $\phi 1(\omega i)$ of the received signal waveform h1 in terms of the angular frequency $\omega i$ can be obtained in the computing unit 59 as follows, $$\phi 1(\omega 1) = \tan^{-1}\{X(\omega i)/R(\omega i)\} \qquad (19)$$

The phase $\phi 1(\omega i)$ is stored in the memory 60 and the phase $\phi 2(\omega i)$ of the received signal waveform h2 is stored in the memory 61. The phase difference $\Delta \phi$ in terms of the angular frequency $\omega i$ of the received signal waveforms h1 and h2 is calculated in the computing unit 62 using the following equation.

$$\Delta \phi(\omega i) = \phi 2(\omega i) - \phi 1(\omega i) \qquad (20)$$

The phase difference $\Delta \phi(\omega i)$ is stored in the memory 64. The phase difference $\Delta \phi(\omega i)$ indicates the phase characteristic of a propagation existing between the reflectors R1 and R2 and is data corresponding to $\Delta \phi$ in the equation (14). The computing unit 35 reads the phase difference $\Delta \phi$ corresponding to the angular frequencies $\omega 1, \omega 1 + \Delta \omega, \omega 2, \omega 2 + \Delta \omega$ from the memory 64 to compute the variation of the phase difference, i.e., dispersion data $\Delta \Delta \phi$ as follows.

$$\Delta \Delta \phi(\omega 1) = \Delta \phi(\omega 1 + \Delta \omega) - \Delta \phi(\omega 1)$$

$$\Delta \Delta \phi(\omega 2) = \Delta \phi(\omega 2 + \Delta \omega) - \Delta \phi(\omega 2) \qquad (21)$$

$\Delta \Delta \phi(\omega 1)$ and $\Delta \Delta \phi(\omega 2)$ are stored in the memory 66. The velocity ratio data $R\phi$, i.e., the ratio of $\Delta \Delta \phi(\omega 1)$ and $\Delta \Delta \phi(\omega 2)$ stored in the memory 66, is obtained in the computing unit 67 in accordance with division in the equation (16). The ratio $R\phi$ is stored in the memory 69 in respective stages of the heating of the body 38 to be examined. The computing unit 70 performs the calculation to know the variation state of the value of $(R\phi - 1)$ on the basis of the values of the velocity ratio data $R\phi$ stored in the memory 69. For example, the temperature variation of slope of frequency dependent attenuation $\beta$ in attenuation can be obtained by dividing the value of $(R\phi - 1)$ on heating by the value of $(R\phi - 1)$ on the ordinary temperature, that is, $$\frac{R\phi - 1 \text{ (heating)}}{R\phi - 1 \text{ (ordinary temp.)}} = \frac{\text{(heating)}}{\text{(ordinary temp.)}} \qquad (22)$$

The results obtained in the temperature variation computing section 71 is shown on the display section 36.

The dispersion data $\Delta \Delta \phi$ in the equation (21) is very small amount. In order to improve the precision it is appropriate to obtain $\Delta \Delta \phi(\omega 1)$ by averaging $\Delta \Delta \phi$ obtained using many different frequencies in the vicinity of $\omega 1$. Similarly, $\Delta \Delta \phi(\omega 2)$ may be obtained. Furthermore, for the purpose of improvement of precision, it is also appropriate to obtain $\Delta \Delta \phi$ using $\Delta \phi(\omega 1)$ and $\Delta \phi(\omega + \Delta \omega)$ newly determined by performing linear approximation in terms of the interval of $\Delta \phi(\omega 1)$ to $\Delta \phi(\omega + \Delta \omega)$. In addition, it is proper to perform the discrete Fourier transformation in terms of the result obtained by repeating transmitting and receiving of the ultrasonic wave and taking the average.

As obvious from the above description, according to this embodiment of the invention, the phase difference $\Delta \phi$ of waveforms in different window intervals is obtained in the phase difference computing section 63 by performing the discrete Fourier transformation the received signal waveforms with respect to a plurality of window intervals. Then, the velocity ratio data $R\phi$ is obtained on the basis of the dispersion data $\Delta \Delta \phi$, i.e., the variation of the phase difference, to detect the variation of dispersion characteristic of acoustic phase velocity resulting from the increase in temperature within the body to be examined. Furthermore, if the temperature dependence of acoustic phase velocity dispersion is previously known, it is possible to estimate the variation in temperature. In addition, when it is arranged to two-dimensional scan the window interval, it is possible to obtain a two dimensional distribution in terms of the temperature variation within the body to be examined.

Figure 4:
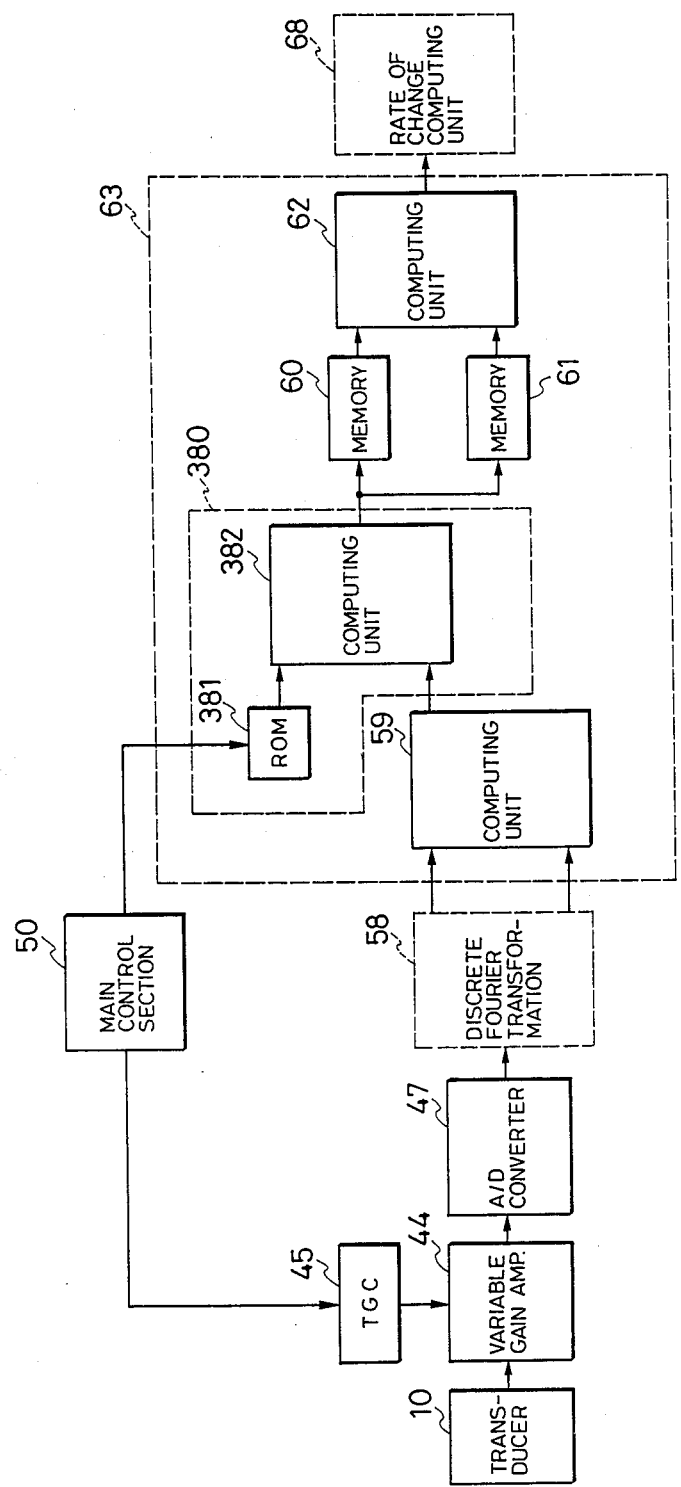
FIG. 4 is a block diagram showing an ultrasonic measuring apparatus according to a third embodiment of the present invention.

FIG. 4 is a block diagram showing a phase difference computing section and its associated portions in a third embodiment of the present invention. The difference between the arrangements of FIG. 3 and FIG. 4 is that the output of the computing unit 59 is coupled to a phase correction section 380 in order to correct the propagation delay time difference of the variable gain amplifier 44.

Numeral 381 represents a ROM which outputs the gain A of the variable gain amplifier specified by the main control section 50 and the delay phase $\phi d$ corresponding to the angular frequency $\omega$. In a computing unit 382, the delay phase $\phi d$ from the ROM 381 is subtracted from the phase outputted from the computing unit 59, and the corrected phase $\phi$, which is the output of the computing unit 382, is written in the memory 60 or 61 in conformity with the window interval. The other arrangement is similar to that of FIG. 3.

A description of operation of the above-mentioned arrangement will be made hereinbelow.

The received signal from the ultrasonic transducer 10 is compensated for the attenuation of the ultrasonic wave within the body 38 in the variable gain amplifier 44. For example, in the case of the variable gain amplifier in which the gain is controlled in accordance with voltage, it is generally known that there is a method in which the gain for the received signal from a deep portion within the body 38 is relatively rendered greater as compared with that for the received signal from a shallow portion therewithin in response to the TGC 45 outputting voltage varied in accordance with time. However, Generally, it is also known that the propagation delay time of a signal is varied in accordance with the variation in the gain of an amplifier. Although this time variation is very small, it is impossible to disregard the amount when the slight variation of acoustic velocity is measured. It is rendered possible to compensate for the affection of the propagation delay time by in advance obtaining the relationship between the gain of the variable gain amplifier 44 at a plurality of window intervals in the discrete Fourier transformation and the delay phase determined in accordance with the propagation delay time corresponding to the gain. The relation between the delay time D and the delay phase $\phi d$ is expressed as follows.

$$\phi d = D \cdot \omega$$

It is understood that the delay phase greatly depends upon the angular frequency. By subtracting the delay phase $\phi d$ from the phase $\phi$ outputted by the computing unit 59, it is made possible to compensate for the affection of the propagation delay time D of the variable gain amplifier 44 to the phase $\phi$ of the received signal waveform.

As obvious from the above description, according to this embodiment, the measurement precision of the phase $\phi$ can be improved by compensating for the affection of the propagation delay time of the variable gain amplifier 44 to the received signal in the phase correction section 380.

Figure 5:
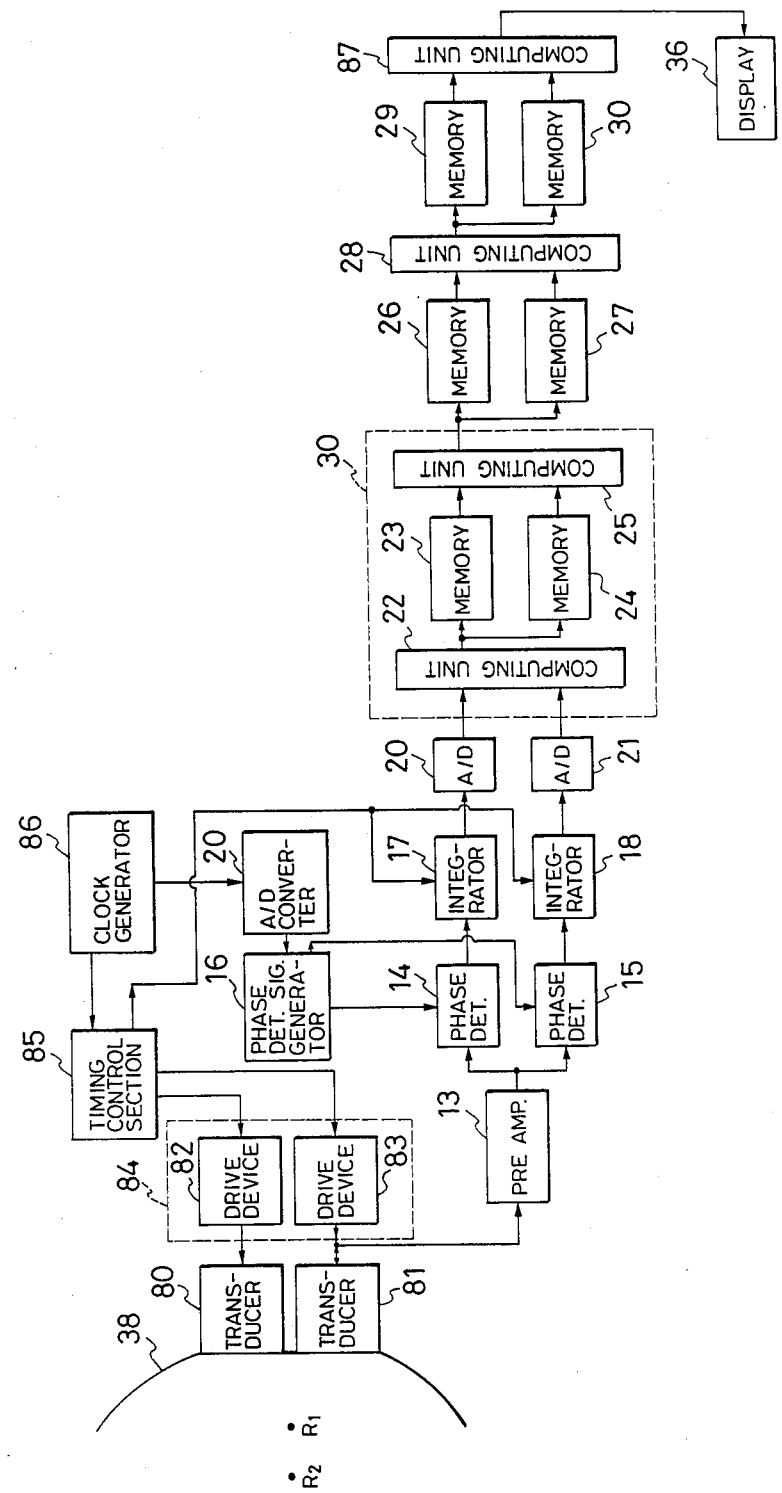
FIG. 5 is a block diagram showing an ultrasonic measuring apparatus according to a fourth embodiment of the present invention.

FIG. 5 is a block diagram showing an ultrasonic diagnostic apparatus according to a fourth embodiment of the present invention.

In FIG. 5, numeral 80 represents a low frequency side ultrasonic transducer, numeral 81 designates a high frequency side ultrasonic transducer, numeral 82 is a pulse drive device for driving the low frequency side ultrasonic transducer 80, numeral 83 is a pulse drive device for driving the high frequency side ultrasonic transducer 81, numeral 84 is a pulse drive section comprising the pulse drive devices 82, 83, numeral 85 represents a timing control section for specifying the operation timing of the pulse drive section 84, numeral 86 designates a clock generator for supplying a clock to the timing control section 85, and numeral 87 is a computing unit for computing the relative rate of change of phase shift. Other portions are identical to those of FIG. 2.

A description of operation of the above-mentioned arrangement will be made hereinbelow.

Figure 6:
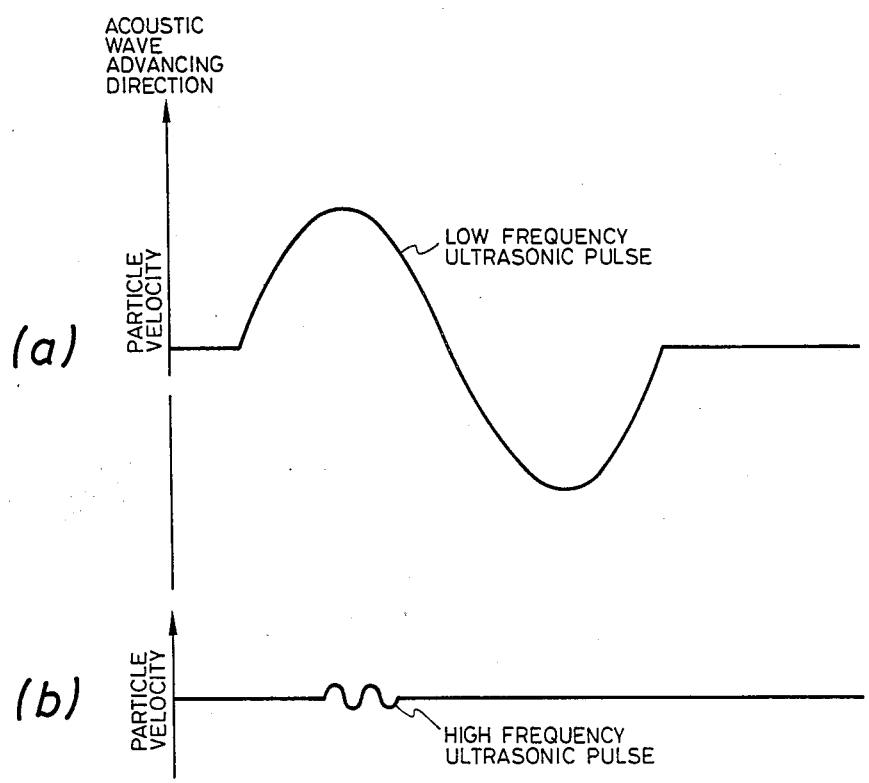
FIG. 6 is a diagram illustrating the phase relation between low frequency ultrasonic wave and high frequency ultrasonic wave.

FIG. 6 shows the phase relation within the body 38 between the respective particle speed waveforms of the ultrasonic pulse outputted from the low frequency side ultrasonic transducer 80 under the condition a of the pulse drive section 84 and the ultrasonic pulse outputted from the high frequency side ultrasonic transducer 81. The ultrasonic pulse of the low frequency side is, for example, of 0.5 MHz and the ultrasonic pulse of the high frequency side is, for example, of 5 MHz, and the central frequencies are significantly different from each other. The high frequency side pulse is outputted when the direction of the particle speed of the low frequency side pulse is coincident with the ultrasonic wave advancing direction within the body 38. The main response portion of the high frequency side pulse is within half-cycle of the low frequency side pulse. On the other hand, in the condition b, the high frequency side pulse is outputted when the particle speed direction of the low frequency side pulse is reverse to the ultrasonic wave advancing direction within the body 38.

A description will be made hereinbelow in terms of how the ultrasonic pulse outputted under such phase and frequency relation is propagated within the body 38 to be examined.

The ultrasonic pulse with power level employed for general ultrasonic diagnostic apparatus is propagated with speed C which is different from the propagation speed Co of infinitesimally small amplitude ultrasonic wave. The relation is expressed as follows.

$$C = Co + \left(1 + \tfrac{1}{2}\tfrac{B}{A}\right) \cdot u = Co + \Delta C \tag{24}$$

where B/A is a non-linear parameter of a medium and is varied in accordance with tissue. For example, it is about 6. Co in organism is about 1500 m/sec and particle speed u is 12 cm/sec when the ultrasonic power is 1 w/cm².

In FIG. 6, the increase $\Delta C$ in the propagation speed of the high frequency side ultrasonic pulse is about 50 cm/sec. Although the relatively changing amount $\Delta C/Co$ of this propagation speed is as little as abount 0.03%, it is possible to perform the accurate detection on the basis of the little changing amount in accordance with precise phase detection techniques.

The process for the phase detection echo produced when the high frequency side pulse outputted under the relation shown in FIG. 6 is reflected by the reflectors R1 and R2 will be hereinbelow described.

The echo is converted in the high frequency side ultrasonic transducer 81 into an electric signal, which is in turn amplified in the preamplifier 13 and phase-detected with 5 MHz in the phase detectors 14, 15. Quadrature signals cos and sin of 5 MHz are generated in the quadrature detection signal generating section 16. The output PC of the phase detector 14 is integrated at the interval of a gate pulse g in the integrator 17 and the output IC of the integrator 17 is converted into a digital amount DC in the A/D converter 20. The output PS of the phase detector 15 is integrated in th integrator 18 and the output IS of the integrator 18 is converted into a digital amount DS in the A/D converter 21. Assuming that the digital amounts DC and DS are the real part and imaginary part of a complex number as shown by the equation, that is, $$Z = DC + jDS \tag{25}$$

the phase angle $\phi$ of Z is the phase difference between the received echo and quadrature phase detection signal. The phase angle $\phi$ is calculated in the computing unit 22. The phase angle $\phi 1$ corresponding to a first timing of the gate pulse signal g is due to the reflector R1 and the phase angle $\phi 2$ corresponding to a second timing thereof is due to the reflector R2.

The phase angle $\phi 1$ is stored in the memory 23 and the phase angle 2 is stored in the memory 24, and the phase difference $\Delta \phi = \phi 1 - \phi 2$ is calculated in the computing unit 25. On the other hand, assuming that the distance between the reflectors R1 and R2 is $\Delta x$, the phase difference $\Delta\phi$ is expressed by the following equation.

$$\Delta\phi = \frac{\omega}{C}\Delta x + \frac{\omega}{C_o}\Delta x \quad (26)$$

where $\omega$ is the angular frequency of the quadrature phase detection signal.

Assuming that the phase difference in the condition a of the pulse drive section 84 is indicated with $\Delta\phi a$ and the phase difference in the condition b thereof is indicated with $\Delta\phi b$, the phase difference $\Delta\phi a$ is stored in the memory 26 and the phase difference $\Delta\phi b$ is stored in the memory 27. The phase shift $\Delta\Delta\phi$, i.e., the difference between the phase differences $\Delta\phi a$ and $\Delta\phi b$, is calculated in the computing unit 28 as follows.

$$\Delta\Delta\phi = \Delta\phi a - \Delta\phi b \quad (27)$$

A description in terms of estimating the varying condition of the phase shift $\Delta\Delta\phi$ caused by the variation of the condition of the pulse drive section 84 will be made hereinbelow.

Assuming that the propagation speed of the high frequency side pulse in the condition a is $C_o + \Delta C$ and the propagation speed of the high frequency side pulse in the condition b is $C_o - \Delta C$, the phase shift $\Delta\Delta\phi$ can be expressed in accordance with the following equation.

$$\Delta\Delta\phi = \frac{\omega}{C_o + \Delta C}\Delta x - \frac{\omega}{C_o - \Delta C}\Delta x \quad (28)$$
$$= \frac{\Delta C \cdot \omega}{C_o} \cdot \frac{2\Delta x}{C_o} = \frac{\Delta C \cdot \omega}{C_o} \cdot \Delta t$$

where $\Delta t$ is a time taken for going and coming back of the infinite small amplitude ultrasonic wave between the reflectors R1 and R2. When $\Delta x$ is 1 cm and $\Delta C/C_o$ is 0.01%, $\Delta\Delta\phi$ becomes about 0.04 radian which is a value detectable sufficiently. The equation (28) is expressed as follows using the non-linear parameter B/A in the equation (24).

$$\Delta\Delta\phi = \left(1 + \frac{1}{2} \cdot \frac{B}{A}\right) u \cdot \frac{\omega}{C_o} \Delta t \quad (29)$$

Thus, since the phase shift $\Delta\Delta\phi$ depends upon the non-linear paramenter B/A, it is possible to measure the variation of the non-linear parameter B/A on the basis of the phase shift $\Delta\Delta\phi$. Since the non-linear parameter B/A depends upon temperature, it is possible to estimate the variation of tempeature within the body 38 on the basis of the phase shift $\Delta\Delta\phi$.

Asdsuming that the phase shift before heating of the body 38 is expressed by $\Delta\Delta\phi N$ and the phase shift after the heating is expressed by $\Delta\Delta\phi H$, $\Delta\Delta\phi N$ is stored in the memory 29 and the $\Delta\Delta\phi H$ is stored in the memory 30, and the rate of change R of $\Delta\Delta\phi N$ relative to $\Delta\Delta\phi H$ can be obtained in the computing unit 38 as follows.

$$R = \frac{\Delta\Delta\phi H}{\Delta\Delta\phi N} \quad (30)$$

The rate of change R is indicated on the display section 36. The indication of the rate of change R can be made in terms of numeric data, brightness variation, hue variation and so on. Furthermore, if the relation between the rate of change R and the temperature variation is known, it is possible to obtain the temperature variation in accordance with inverse operation and it is appropriate to indicate the result.

In the above description, the two integrators 17 and 18 are provided corresponding to the phase detectors 14 and 15. However, in the case that the timings of integration become close to each other, it is appropriate that a plurality of integrators are provided for the output of each the phase detector and the outputs of the integrators is selected by a multiplexer and A/D-converted.

As obvious from the above description, according to this embodiment, the phase difference $\Delta\phi$ between the echoes due to the reflectors R1 and R2 within the body 38 is obtained by changing the condition of the pulse drive section 84, and the relative rate of change R of the phase shift $\Delta\Delta\phi$ can be obtained by obtaining the variation of the phase difference $\Delta\phi$, i.e., phase shift $\Delta\Delta\phi$ before and after heating of the body 38 and the temperature variation can be obtained. When the non-linear parameter B/A or the relative rate of change is already known, it is possible to estimate the increase in temperature within the body resulting from the heating.

Figure 7:
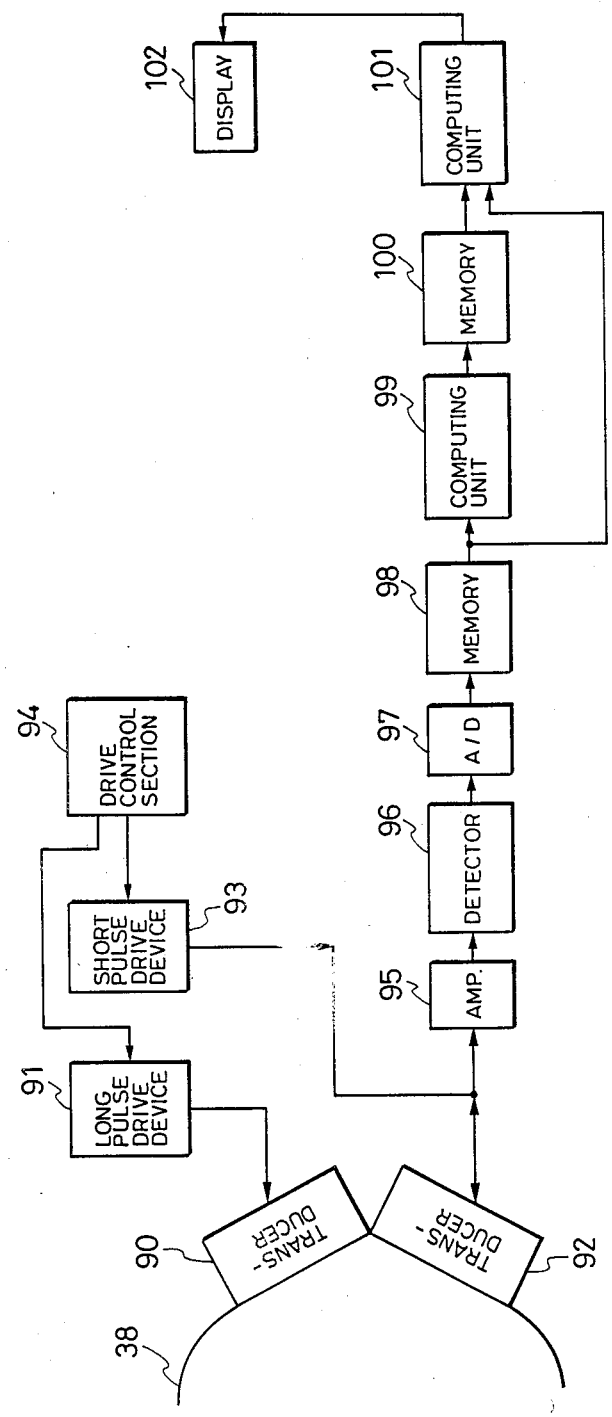
FIG. 7 is a block diagram showing an ultrasonic measuring apparatus according to a fifth embodiment of the present invention.

FIG. 7 is a block diagram showing an ultrasonic diagnostic apparatus according to fifth embodiment of the present invention.

In FIG. 7, numeral 90 represents a low frequency side ultrasonic transducer, numeral 91 designates a long pulse drive device for driving the ultrasonic transducer 90, numeral 92 is a high frequency side ultrasonic transducer, numeral 93 is a short pulse drive device for driving the ultrasonic transducer 92. A drive control section 94 controls the pulse width and output amplitude of the long pulse drive device 92, the operating timing of the short pulse drive device 93. A long pulse generating means comprises the ultrasonic transducer 90 and the long pulse drive device 91 and a short pulse generating means comprises the ultrasonic transducer 92 and the short pulse drive device 93. Numeral 95 is an ampliofier for amplifier the received signal from the high frequency side ultrasonic transducer 92, numeral 96 represents a detector for envelope-detecting the output of the amplifier 95, numeral 97 designates an A/D converter for converting the output of the detector 96 into a digital signal, numeral 98 is a memory for storing the output of the A/D converter 97, numeral 99 depicts a computing unit for performing devision in terms of the data stored in the memory 98, numeral 100 is a memory for storing the output of the computing unit 99, numeral 101 is a computing unit for performing division in terms of the data stored in the memory 100 under the condition of different temperatures of the body 38 to be examined, and numeral 102 designates a display section for indicating the output of the computing unit 101.

A description of operation of the above-mentioned arrangement will be made hereinbelow.

Figure 8:
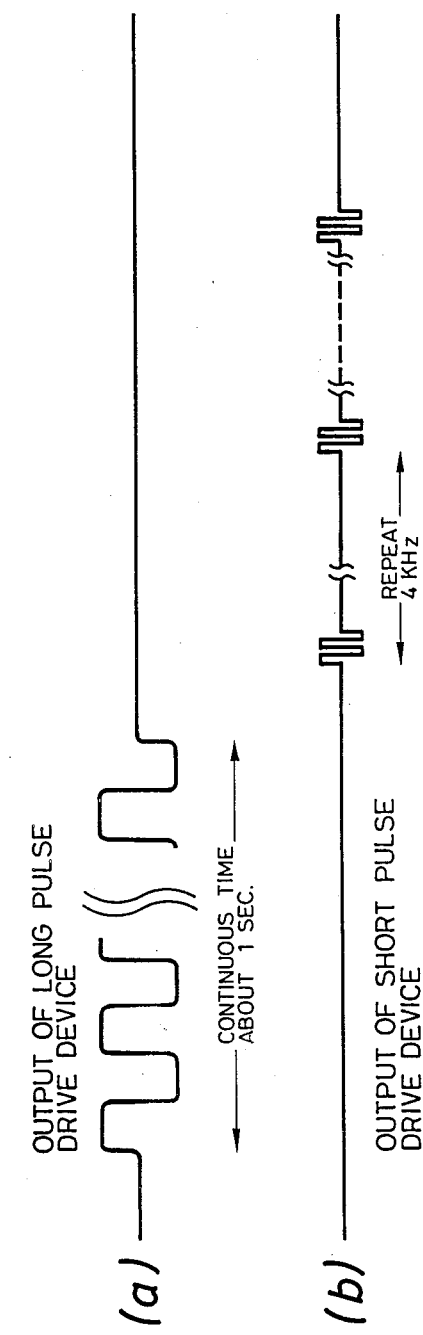
FIG. 8 is a timing diagram showing the operating timings of the ultrasonic transducer of FIG. 7.

First of all, the long pulse drive device 91 applies a RF pulse with, for example, the frequency of 500 KHz and burst length of about 1 sec to the low frequency side ultrasonic transducer 90. After the termination of the operation of the long pulse drive device 91, the short pulse drive device 93 applies a short RF pulse with, for example, 3.5 MHz and two cycles to the high frequency side ultrasonic transducer 92. The short RF pulse, for example, is continued with repeated period of about 4 KHz for several seconds. Example of the operation of the long pulse drive device 91 and short pulse drive device 93 is shown in FIG. 8. the scatterers within th body 38 is emitted by the ultrasonic wave for about 1 second in response to the operation of the low frequency side ultrasonic transducer 90, and the positions of these scatterers are shifted from the equilibrium state and the phenomenon such as orientation is indicated. As the application of the phenomenon such as orientation, there is an ultrasonic detecting device, so-called poleman cell which has been disclosed, for example, in "BIOMEDICAL ULTRASONICS" (page 93) written by P. N. T. WELLS and published by Academic Press in 1977. This poleman cell uses the principle in which metal pieces of about 20 microns in diameter and of 1.5 microns in thickness drifted in liquid is stood in a row in a direction in repsonse to the emitting of an ultrasonic wave and an optical variation occurs. In detail, in the case of an ultrasonic magnitude of 0.1 mw/cm², the brightness is varied by about 50% after 1 to 5 seconds.

Based on the above-mentioned phenomenon, the position of a scatterer within the body 38 to be examined is shifted from the equilibrium state and returns to the equilibrium state after the termination of operation of the long pulse drive device 91. The shift of the position of the scatterer from the equilbrium state is detected as the variation of reflection characteristic of ultrasonic wave. The variation of the reflection characteristic in accordance with time after the operation stop of the long pulse drive device 91 is detected by the high frequency side ultrasonic transducer 92 as the variation in the received signal level per the driving of the short pulse drive device 93. The received signal thus varied is amplified in the amplifier 95, is envelope-detected in th detector 96, is converted into a digital signal in the A/D converter 97, and then stored in the memory 98. It is proper that the time taken until the position of the scatterer within the body 38 returns to the equilbrium state is relaxative, and the time depends upon temperature within the body 38 to be examined. Therefore, by measuring the rate of change with the passage of time in terms of data corresponding to a specific depth x with the body 38 among the data D of the reflection signals stored in the memory 98 in synchronism with the drive timing of the short pulse drive device 93, it is possible to obtain information relating to the temperature of its portion. The rate of change R with the passage of time, for example, can be expressed by as follows.

$$R = \frac{D(n \Delta t, x)}{D(0, x)} \quad (31)$$

where n is positive integer and $\Delta t$ is time interval for the driving of the short pulse driving device 92. The rate of change of temperature V shown before and after the heating of a body to be examined is expressed as follows.

$$V = \frac{R \text{ (after heating)}}{R \text{ (before heating)}}$$

If the temperature dependence of the rate of change of temperature V is already known with respect to the body 38 to be examined, it is possible to estimate the temperature variation within the body on the basis of the value of V.

According to this embodiment, information relating to the temperature variation within the body can be obtained by measuring the change with the passage of time in terms of the reflection signal from a specific depth within the body, and it is possible to obtain accurate information relating to the temperature variation even if the path of the ultrasonic wave propagated in the body is refracted complicatedly.

Although in the above description the the rate of change R with the passage of time in terms of the reflection signal has been defined in accordance with the equation (31), it is allowed to be defined in accordance with different equation. For example, when the scattering coefficient at the time that the scatterer within the body is in the equilibrium state is DS(x), the rate of change with the passage of time can be defined in accordance with the following equation.

$$R = \frac{D(N \cdot \Delta t, x) - DS(x)}{D(0, x) - DS(x)} \quad (32)$$

DS(x) is the output of the A/D converter 97 corresponding to the received signal obtained in response to the actuation of the short pulse driving device 93 for the time period of about one second before the actuation of the long pulse driving device 91 or after the termination of the actuation thereof, and is stored in the memory 98. The subtraction in the equation (32) may be performed by the computing unit 99.

Figure 9:
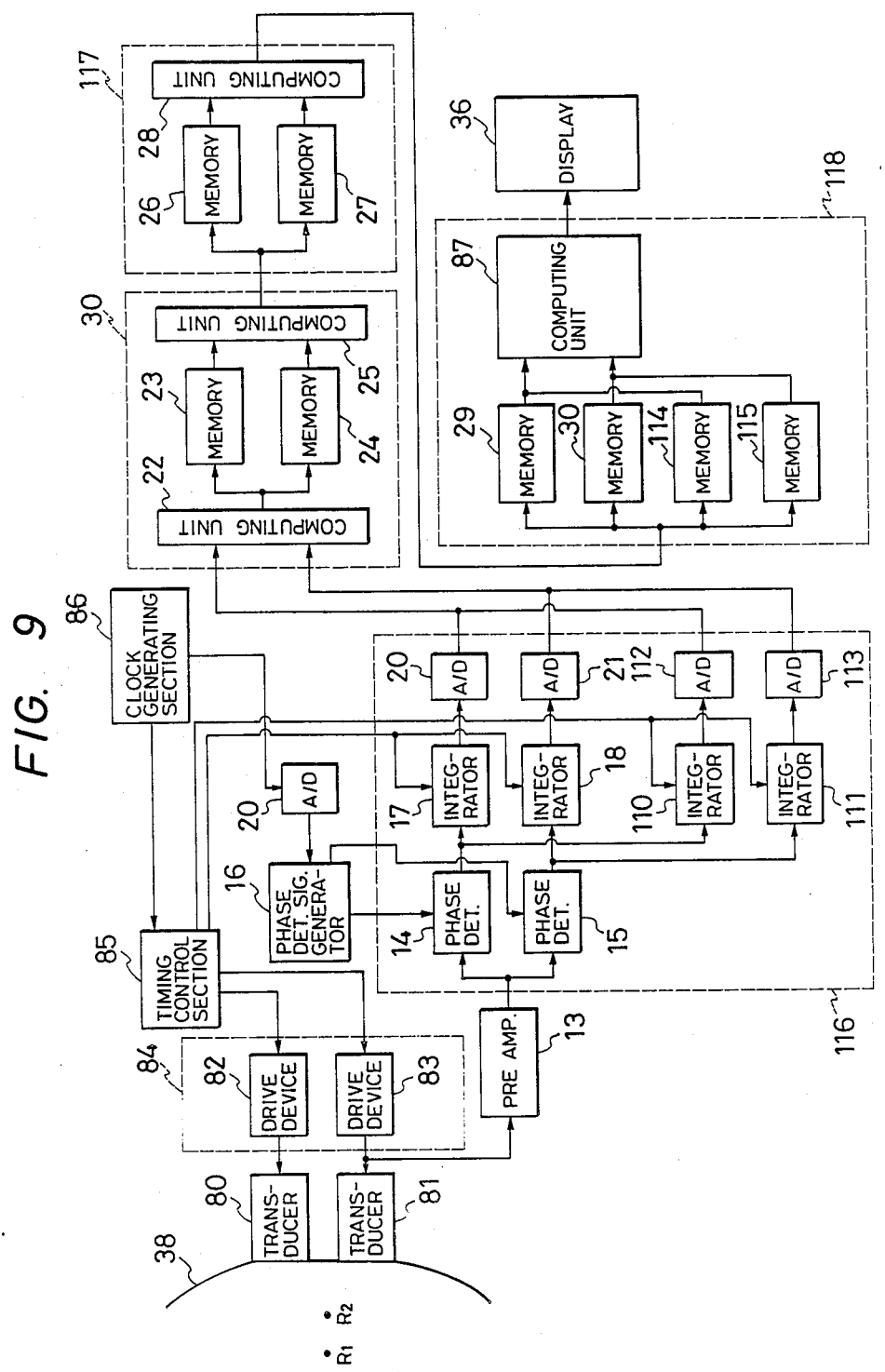
FIG. 9 is a block diagram showing an ultrasonic measuring apparatus according to a sixth embodiment of the present invention.

FIG. 9 is a block diagram showing an ultrasonic diagnositic apparatus according to a sixth embodiment of the present invention.

This embodiment is similar to the FIG. 5 embodiment with exception that the output of the phase detector 14 is supplied to an integrator 110 in addition to the integrator 17 and the output of the phase detector 15 is supplied to an integrator 111 as well as the integrator 18, and the outputs of the integrators 110 and 101 are respectively applied through A/D converters 112 and 113 to the computing unit 22, and further the output of the computing unit 28 is supplied to memories 114 and 115 in addition the memories 29 and 30 and the outputs of the memories 114 and 115 are supplied to computing unit 87. Numeral 116 represents a phase detection means, numeral 117 designates a phase shift computing means, and numeral 118 is an elimination computing section. Parts corresponding to those in FIG. 5 are marked with the same numerals.

A description of the operation of the above arrangement will be made hereinbelow.

The phase relation of particle speed waveforms of the ultrasonic pulse outputted by the low frequency side ultrasonic transducer 80 and the ultrasonic pulse outputted by the high frequency side ultrasonic transducer 81 when the pulse drive section is in the state a is shown in FIG. 6. The low frequency side ultrasonic pulse is, for example, of 0.25 MHz and the high frequency ultrasonic pulse is, for example, of 2.5 MHz, and the central frequencies are considerably different from each other.

In the case of peak ultrasonic output level used in general ultrasonic diagnostic apparatus, the propagation speed of the ultrasonic pulse is varied between the top portion and bottom portion of the pulse waveform. This relation is expressed as follows as well as the equation (24).

$$C = Co \pm \left(1 + \tfrac{1}{2}\frac{B}{A}\right)u = Co \pm \Delta C \quad (33)$$

Until the echoes from the reflectors R1 and R2 are phase-detected by the phase detectors 14 and 15, this embodiment is similar to the FIG. 5 embodiment.

Frequency f is selected from frequencies, for example, 1.5 to 3 MHz in the vicinity of the high frequency side drive frequency 2.5 MHz.

The quadrature phase detection signal generating section 16 is synchronized with the phase control section 20 which is in turn synchronized with the clock generating section 86. It is appropriate that the phase control section is arranged using an available synthesizer.

Figure 10:
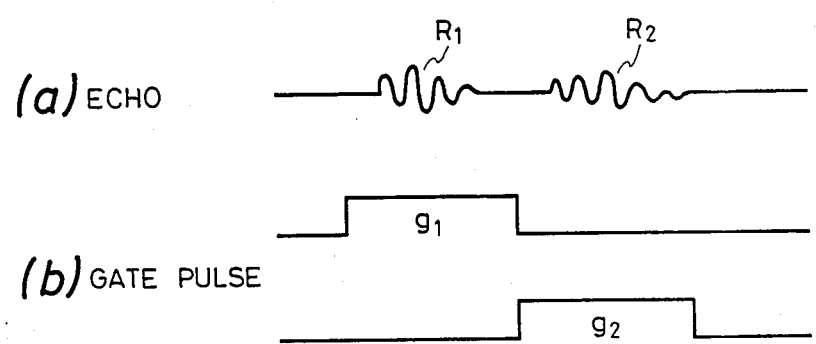
FIG. 10 is a diagram showing the timing relation between gate pulse and echo.

The output of the phase detector 14 is integrated by the integrator 17 with the timing of the gate pulse signal g1 and the output of the phase detector 15 is integrated by the integrator 18. The output of the phase detector 14 is integrated by the integrator 110 with the timing of the gate pulse signal g2 and the output of the phase dector 15 is integrated by the integrator 111. The outputs of the phase detectors 17 and 18 are respectively converted into digital amounts DC and DS in the A/D converters 20 and 21. As in the case of the equation (25), assuming that the digital amounts DC and DS are the real part and imaginary part of a complex number, the phase angle $\phi$ of the complex number Z is the phase difference relative to the phase detection signal relating to frequency f component of the received signal. The phase angle $\phi$ is computed in the computing unit 22. Similarly, the phase angle is calculated in terms of the outputs of the A/D converters 112 and 113. The phase angle $\phi 1$ corresponding to the timing of the gate pulse signal g1 is due to the reflector R1 and the phase angle $\phi 1$ corresponding to the timing of the gatepulse signal g2 is due to the reflector R2. The timing relationship between the echoes from the reflectors R1, R2 and the gate pulse signals g1, g2 is shown in FIG. 10. The phase angle $\phi 1$ is stored in the memory 23 and the phase angle $\phi 2$ is stored in the memory 24, the phase difference $\Delta \phi = \phi 1 - \phi 2$ is calculated in the computing unit 25.

On the other hand, the distance between the reflectors R1 and R2 can be expressed by $\Delta x(\omega)$. Here, the reason that the distance $\Delta x$ is a function of the angular frequency $\omega (=2\pi \cdot f)$ is that, when the ultrasonic reflection coefficient of the reflectors R1 and R2 is varied in accordance with frequency, it is impossible to fix that the substantial reflecting surfaces of these reflectors are points of minimum distance from the ultrasonic transducer. Therefore, the distance $\Delta x$ between the substantial acoustic reflecting surfaces on the reflectors R1 and R2 is indicated as a function of the angular frequency $\omega$. By using the distance $\Delta x(\omega)$ which is an unknown amount, the phase difference $\Delta \phi(\omega)$ can be expressed in accordance with the following equation.

$$\Delta\phi(\omega) = \frac{\omega}{C(\omega)} \Delta x(\omega) - \frac{\omega}{Co(\omega)} \Delta x(\omega) \qquad (34)$$

Here, the reason that the phase velocities Co and C are expressed as a function of the angular frequency $\omega$ is to make clear that the phase velocity has distribution characteristic. This distribution characteristic will be hereinafter described in detail.

When the phase difference in the condition a of the pulse drive section 84 is $\Delta\phi a$ and the phase difference in the condition b thereof is $\Delta\phi b$, the phase difference $\Delta\phi a$ is stored in the memory 26 and the phase difference $\Delta\phi b$ is stored in the memory 27. The difference between the phase difference $\Delta\phi a$ and the phase difference $\Delta\phi b$, i.e., phase difference variation $\Delta\Delta\phi$ is calculated as follows in the computing unit 28.

$$\Delta\Delta\phi = \Delta\phi a - \Delta\phi b \qquad (35)$$

When the phase velocity of the high frequency side pulse in the condition a of the pulse drive section 84 is $Co + \Delta C$ and the phse velocity in the condition b thereof is $Co - \Delta C$, the phase difference variation $\Delta\Delta\phi$ is expressed by the following equation.

$$\Delta\Delta\phi(N, \omega) = \frac{\omega}{Co + \Delta C} \Delta x - \frac{\omega}{Co - \Delta C} \Delta x \qquad (36)$$
$$\approx \frac{\Delta C \cdot \omega}{Co} \cdot \frac{2\Delta x}{Co} = \frac{\Delta C \cdot \omega}{Co} \cdot \Delta t$$

where $\Delta t$ is time taken for going and coming back of the infinite small amplitude ultrasonic wave between the reflectors R1 and R2. Parameter N represents that this phase shift occurs due to non-linear phenomenon. The equation (36) is rewritten as follows using the non-linear parameter B/A used in the equation (1).

$$\Delta\Delta\phi(N, \omega) = \left(1 + \tfrac{1}{2} \cdot \frac{B}{A}\right) u \cdot \frac{\omega}{Co(\omega)} \cdot \Delta t(\omega) \qquad (37)$$

The delay time $\Delta t(\omega)$ used in the equation (33) is the amount which can be measured, as indicated hereinbelow, it is possible to show the ratio of the phase velocity with known amount if the phase shifts $\Delta\phi$ are obtained with respect to the angular frequencies $\omega 1$ and $\omega 2$ and its ratio is calculated.

$$\frac{\Delta\Delta\phi(N, \omega 1)}{\Delta\Delta\phi(N, \omega 2)} = \frac{Co(\omega 2) \cdot \omega 1 \cdot \Delta t(\omega 1)}{Co(\omega 1) \cdot \omega 2 \cdot \Delta t(\omega 2)} \qquad (38)$$

$$\frac{Co(\omega 2)}{Co(\omega 1)} = \frac{\omega 2 \cdot \Delta t(\omega 2) \cdot \Delta\Delta\phi(N, \omega 1)}{\omega 1 \cdot \Delta t(\omega 1) \cdot \Delta\Delta\phi(N, \omega 2)} \qquad (39)$$

The method of obtaining the delay time $\Delta t(\omega)$ will be described hereinbelow.

First of all, only the high frequency side pulse drive device 83 is energized in the condition that the low frequency side pulse drive device 82 is stopped and the received signals are phase-detected with the angular frequency $\omega$ in the phase detectors 14 and 15, and then as well as in the method described above, the phase angle $\phi 1$ of the received signal due to the reflector R1 is stored in the memory 23 and the phase angle $\phi 2$ of the received signal due to the reflector R2 is stored in the memory 24. Thereafter, the phase difference $\Delta\phi(\omega)$ is obtained in the computing unit 25 and is stored in the memory 26. The phase difference $\Delta\phi(\omega)$ can be expressed in accordance with the following equation.

$$\Delta\phi(\omega) = \frac{2 \cdot \Delta x(\omega)}{Co(\omega)} \cdot \omega \qquad (40)$$

Secondly, the received signal is phase-detected with angular frequency $\omega + \Delta\omega$, and the phase difference $\Delta\phi(\omega + \Delta\omega)$ is stored in the memory 27. The variation of frequency for phase detection is performed by changing the frequency generated by the phase control section 20. The dispersion data $\Delta\Delta\phi$, i.e., the difference between the phase differences $\Delta\phi$ resulting from the variation of the frequency for phase detection, is calculated in the computing unit 28 as follows.

$$\Delta\Delta\phi = \Delta\phi(\omega) - \Delta\phi(\omega + \Delta\omega) \tag{41}$$

If the variation of the angular frequency $\Delta\omega$ is small, the dispersion data $\Delta\Delta\phi$ is approximated in the following equation.

$$\Delta\Delta\phi(\Delta\omega, \omega) = \frac{2 \cdot \Delta x(\omega)}{Co(\omega)} \cdot \omega - \frac{2 \cdot \Delta x(\omega + \Delta\omega)}{Co(\omega + \Delta\omega)} \cdot \tag{42}$$

$$(\omega + \Delta\omega) \simeq \frac{2 \cdot \Delta x(\omega)}{Co(\omega)} \cdot \Delta\omega = \Delta t(\omega) \cdot \Delta\omega$$

Here, the parameter $\Delta\omega$ represents that this phase shift occurs due to the variation of the phase detection frequency. From the above equation, the delay time $\Delta t(\omega)$ can be expressed in accordance with the following equation.

$$\Delta t(\omega) = \frac{\Delta\Delta\phi(\Delta\omega, \omega)}{\Delta\omega} \tag{43}$$

By using the equation (43), the equation (39) representing the ratio of phase velocity can be expressed by the following equation, comprising the amounts which can be measured.

$$\frac{Co(\omega 2)}{Co(\omega)} = \frac{\omega 2 \cdot \Delta\Delta\phi(\Delta\omega, \omega 2) \cdot \Delta\Delta\phi(N, \omega 1)}{\omega 1 \cdot \Delta\Delta\phi(\Delta\omega, \omega 1) \cdot \Delta\Delta\phi(N, \omega 2)} \tag{44}$$

From the above-mentioned relation, it is possible to obtain the ratio of the phase velocity in terms of the different angular frequencies $\omega 1$ and $\omega 2$ in detail.

First, when the angular frequency for phase detection is $\omega 1$, the ultrasonic wave is transmitted and received in the condition a of the pulse drive section, and then the ultrasonic wave is transmitted and received in the condition b. The obtained phase shift $\Delta\Delta\phi(N, \omega 1)$ is stored in the memory 29. Secondly, the transmitting and receiving of the ultrasonic wave by only the high frequency side ultrasonic transducer is performed two times in the condition that the low frequency side ultrasonic transducer is deenergized. At the first time, it is phase-detected with the angular frequency $\omega 1$, and at the second time it is phase-detected with the angular frequency $\omega 1 + \Delta\omega$. The obtained phase shift $\Delta\Delta\phi(\Delta\omega, \omega 1)$ is stored in the memory 30. Subsequently, when the angular frequency for the phase detection is $\omega 2$, the transmitting, receiving and phase detection are similarly performed, and the obtained phase shift $\Delta\Delta\phi(N, \omega 2)$ is stored in the memory 114 and $\Delta\Delta\phi(\Delta\omega, \omega 2)$ is stored in the memory 115. In the computing unit 87, the rate of the phase velocity is obtained by performing the calculation indicated in the equation (44) on the basis of the contents of the memories 29, 30, 114 and 115 and the values of the angular frequencies $\omega 1$ and $\omega 2$. It is known that the variation of the phase velocity due to frequency is about 1 m/sec in fat and is about 3 m/sec in muscle, when the distribution characteristic is $\omega 2/\omega 1 = 2$. It is proper selection that $\omega 1 = 2\pi \times 1.5$ MHz and $\omega 2 = 2\pi \times 3$ MHz with respect to the high frequency side frive frequency of 2,5 MHz when $\omega 2/\omega 1$. The ratio $Co(\omega 2)/Co(\omega 1)$ of the phase velocities thus obtained is indicated on the display section 36.

As obvious from the above description, according to this embodiment, by controlling the phase between different frequency drive pulses of the timing control section 85 and pulse drive section 84, the phase shift $\Delta\Delta\phi(N, \omega)$ of the reflection signals based on the non-linear phenomenon of propagation is obtained. Therefater, the phase shift $\Delta\Delta\phi(\Delta\omega, \omega)$ of the reflection signals is obtained by slightly changing the frequency generated from the phase control section 20. With these measurements being performed with the angular frequency $\omega = \omega 1$ and $\omega 2$, the ratio of the phase velocity can be obtained in the elimination computing section 118. Unlike the conventional techniques, since the method is affected by the propagation path, it is possible to accurately obtain data relating to the acoustic velocity of tissue within organism.

Although in the above description the central frequency of the high frequency side pulse drive device 83 is constant, it is appropriate that the central frequency is varied in response to the variation of the frequency for phase detection. Furthermore, it is considered that the obtained data relating to acoustic velocity is indicated concurrently with the B-mode dislocation image. For example, it is appropriate that the gate interval is conformed with the dislocation image and the value of ratio of the phase velocity is indicated with false color at the gate position. Furthermore, for the purpose of improving S/N ratio, it is proper to average the result obtained by measuring the ratio of the phase velocity many times. In addition, with a waveform memory being provided at the rear of the preamplifier 13, it is also possible to perform the calculations and phase detection after many waveforms are stored therein. Furthermore, the two integrators are provided for one phase detector. However, it is possible to optinally select the number of the integrators.

Figure 11:
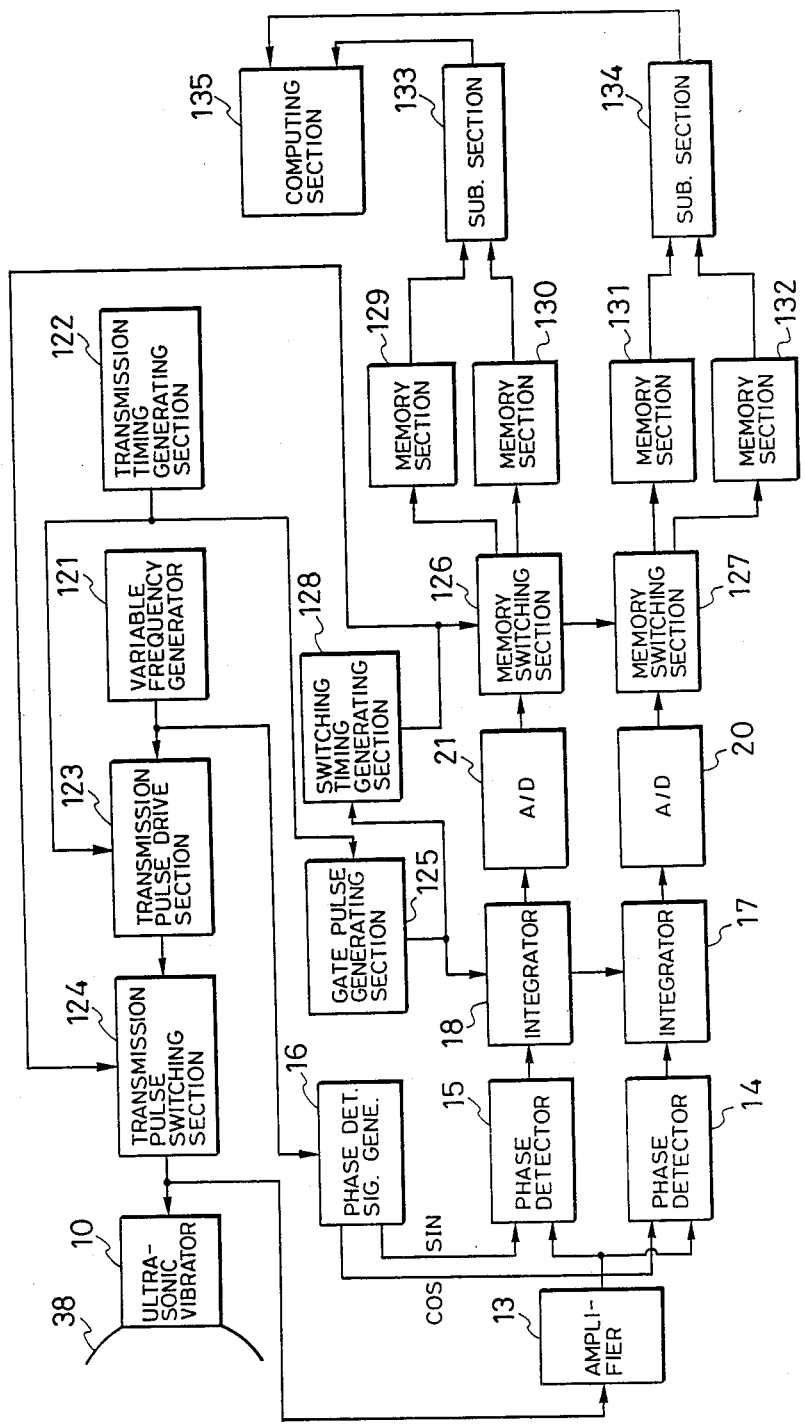
FIG. 11 is a block diagram showing an ultrasonic measuring apparatus according to a seventh embodiment of the present invention.

FIG. 11 is a block diagram showing an ultrasonic diagnostic apparatus according to a seventh embodiment of the present invention.

In FIG. 11, numeral 10 is an ultrasonic vibrator (transducer) for transmitting and receiving ultrasonic wave, numeral 38 is a body to be examined, numeral 121 is a variable frequency generator, numeral 122 represents a transmitting timing generating section for producing a timing of transmission of an ultrasonic wave, numeral 123 designates a transmission pulse drive section for transmitting an ultrasonic wave in synchronism with the transmission timing signal from the transmission timing generating section 122, numeral 124 depicts a transmission pulse switching sectin connected to the transmission pulse drive section 123 for controlling the supply of the ultrasonic driving pulse to the ultrasonic vibrator 10, numeral 13 is an amplifier coupled to the ultrasonic vibrator. Numerals 14 and 15 are phase detectors coupled to the amplifier 13, numeral 16 represents a phase detection signal generating section, connected to the variable frequency generator 121, for supplying a phase detection signal to the phase detecors 14, 15, numeral 18 is an integrator coupled to the phase detector 15, numeral 17 is an integrator connected to the phase detector 14, numeral 125 represents a gate pulse generating section for supplying the integrators 17, 18 with a gate pulse synchronized with the transmission timing pulse signal from the transmission timing generating section 122. Numeral 21 represents an A/D converter coupled to the integrator 18, numeral 20 an A/D converter coupled to the integrator 17, numeral 126 is a memory switching section for switching the output of the A/D converter 21, numeral 127 is a memory switching section for switching the output of the A/D converter 20, numeral 128 is a switching timing generating section, connected to the gate pulse generating section 125, for supplying a switching timing control signal to the transmission pulse switching section 124 and the memory switching sections 126, 127. Numerals 129 and 130 are memory sections coupled to the memory switching section 126, numerals 131, 132 are memory sections coupled to the memory switching section 127, numeral 133 is a subtraction unit coupled to memory sections 129 and 130, numeral 134 is a subtraction unit coupled to the memory sections 131, 132, numeral 135 is a computing unit coupled to the subtraction units 133, 134.

A description of operation of the above arrangement will be described hereinbelow.

The transmission pulse drive section 123 supplies the transmission pulse switching section 124 with an ultrasonic drive pulse of an angular frequency $\omega$ synchronized with a clock fed from the variable frequency generator 121 in synchronism with a transmission timing signal produced in the transmission timing generating section 122. The transmission pulse switching section 124 performs control in terms of outputting the ultrasonic drive pulse to the ultrasonic vibrator 10 or stopping the outputting thereof in response to a switching timing control signal from the switching timing generating section 128. First, it is assumed that the switching timing control signal is outputted. The transmission pulse switching section 124 outputs an ultrasonic drive pulse to the ultrasonic vibrator 10 and an ultrasonic wave produced in the ultrasonic vibrator 10 is transmitted into the body 38 to be examined. The ultrasonic wave reflected within the body 38 is received by the ultrasonic vibrator 10 and is converted into an electric signal, and then supplied through the amplifier 13 to the phase detectors 14, 15. The reflected waves inputted in the phase detectors 14, 15 are quadrature-phase-detected with phase detection signals sin and cos synchronized with a clock from the variable frequency generator 121. The outputs of the phase detectors 14 and 15 are supplied to the integrators 17 and 18 and integrated within the interval of a gate pulse produced in the gate pulse generating section 125 in synchronism with the transmission timing signal from the transmission timing generating section 122, and then converted into digital signals in the A/D converters 20 and 21. The memory switching section 126 supplies the output of the A/D converter 21 to either of memory sections 129 or 130, for example, to the memory section 129 in accordance with the switching timing control signal from the switching timing generating section 128. Similarly, the memory switching section 127 supplies the output of the A/D converter 20 to, for example, the memory section 131. Secondly, the switching timing generating section 128 changes the switching timing control signal so as to perform stopping control. The transmission pulse switching section 124 does not supply the ultrasonic vibrator 10 with the ultrasonic drive pulse, which is the ouput of the transmission pulse drive section 123, in accordance with the switching timing control signal. The output of the ultrasonic vibrator 10 is quadrature-phase-detected as well as in the phase detection method of the reflection wave in the case that the ultrasonic wave is transmitted within the body 38, and the results of the phase detection are stored, for example, in the memories 15 and 132 other than the above-mentioned memories by means of the switching sections 126 and 127. The information included in the results of the phase detection corresponds to unnecessary operation caused by the switching operation and noises produced by the electronic circuits. The subtraction section 133 subtracts the value included in the memory 130 in the case of no the ultrasonic drive pulse from the value included in the memory section 129, i.e., the value included in the reflected wave from the actual body and the result of the subtraction is supplied to the computing section 135. Similarly, the subtraction section 134 subtracts the value of the memory section 132 from the value of the memory section 131 and the result is supplied to the computing unit 135. The computing section 135 allows the phase ($\omega$) to be obtained on the basis of the output values of the subtraction sections 133, 134 in accordance with an equation $(\omega) = \tan^{-1}(OS1/OC1)$. it is possible to further obtain the information relating to nature of tissue by calculating the phase ($\omega$) a series of operations in connection with frequenct variation of the variable frequency generator 121.

It should be understood that the foregoing relates to only preferred embodiments of the invention, and that it is intended to cover all changes and modifications of the embodiments of the invention herein used for the purposes of the disclosure, which do not constitute departures from the spirit and scope of the invention.

What is claimed is:

1. An ultrasonic measuring apparatus comprising:
   ultrasonic transducer means driven in reponse to a plurality of frequencies for receiving ultrasonic waves reflected from a body to be examined and for converting the reflected ultrasonic waves into electric signals;
   phase detecting means for phase-detecting the signal from said ultrasonic transducer means in synchronism with the frequencies;
   timing generator means for generating a plurality of gate intervals in synchronism with the driving of said ultrasonic transducer means; and
   computing means for obtaining phase differences at the plurality of gate intervals for the plurality of frequencies in accordance with an output of said phase detecting means indicative of the result of the phase-detection and for computing a dispersion data, which is a variation component of the phase difference between the frequencies, and the relative variation between the dispersion data.

2. An ultrasonic measuring apparatus as claimed in claim 1, wherein the dispersion data is obtained a plurality of times and the obtained dispersion data is averaged.

3. An ultrasonic measuring apparatus comprising:
   ultrasonic transducer means for receiving an ultrasonic wave reflected from a body to be examined and for converting the reflected ultrasonic wave into an electric signal;
   amplifier means for amplifying the signal from said ultrasonic transducer means;
   discrete Fourier transformation means for performing a discrete Fourier transformation in terms of the output of said amplifier with a plurality of window intervals;
   phase difference computing means for obtaining a phase difference of the output data from said discrete Fourier transformation means in accordance with the plurality of window intervals;
   frequency change rate computing means for obtaining the rate of change of frequency in terms of the output data from said phase difference computing means; and temperature change rate computing means for obtaining the rate of change of temperature on the basis of the obtained rate of change of frequency.

4. An ultrasonic measuring apparatus as claimed in claim 3, wherein said phase difference computing means is arranged so that phase difference is obtained after a phase correction is performed in accordance with the gain level of said amplifier means.

5. An ultrasonic measuring apparatus comprising:
means for generating a plurality of drive pulses whose frequencies are different from each other;
timing control means for controlling phases between the plurality of drive pulses;
ultrasonic transducer means coupled to said drive pulse generating means;
phase detecting means for performing a phase detection in terms of signals from said ultrasonic transducer means;
means for changing the detection frequency of said phase detecting means;
gate interval generating means for generating a plurality of gate intervals in synchronism with said drive pulse generating means;
phase difference computing means for obtaining a phase difference in terms of the outputs of said phase detecting means in accordance with the gate intervals; and
phase shift comprising means for obtaining the difference between the outputs of the phase difference computing means corresponding to different conditions of said timing control means or corresponding to different detection frequencies, 6. An ultrasonic measuring apparatus as claimed in claim 5, further comprising elimination computing means for obtaining the ratio of phase velocities at different frequencies on the basis of said phase shift computing means.

7. An ultrasonic measuring apparatus comprising:
means for generating a low frequency ultrasonic pulse to illuminate a body to be examined;
ultrasonic means for transmitting to a portion of the body illuminated by said low frequency ultrasonic pulse a high frequency ultrasonic pulse, having a frequency higher than that of said lower frequency ultrasonic pulse; and
computing means, obtaining phase differences at a plurality of gate intervals generated for said low and high frequencies, for computing the rate of change in a received signal with the passage of time of an output signal of said ultrasonic transmitting means corresponding to said high frequency ultrasonic pulse with respect to a specific depth within the body.

8. An ultrasonic measuring apparatus comprising:
ultrasonic vibrator means for transmitting and receiving an ultrasonic wave;
transmission timing generating means for generating a transmission timing signal;
transmission pulse means for generating a transmission pulse in synchronism with said transmission timing signal;
gate pulse generating means for generating a gate pulse in synchronism with said transmission timing signal;
switching timing means for generating a switching timing control signal on the basis of said gate pulse;
transmission pulse switching means provided between said ultrasonic vibrator means and transmission pulse means for switching the transmission pulse from said transmission pulse means on the basis of the switching timing control signal;
varaiable frequency generator means coupled to said transmission pulse means;
amplifier means for amplifying the signal corresponding to the wave received by said ultrasonic vibrator;
phase detection signal generating means for generating a phase detection signal in synchronism with a clock from said variable frequency generator means;
first and second phase detectors for quadrature-phase-detecting the output of said amplifier means in accordance with the phase detection signal;
first and second integrators for integrating the outputs of said first and second phase detectors within interval of the gate pulse produced in synchronism with the transmission timing signal;
first and second A/D converters for converting the outputs of said first and second integrators into digital values;
first and second memory sections for receiving the output value of said first A/D converter through first memory switching means controlled in accordance with the switching timing control signal;
first subtraction means for calculating the difference between the outputs of said first and second memory sections;
thrid and fourth memory sections for receiving the output value of said second A/D converter through second memory switching means controlled in accordance with the switching timing control signal;
second subtraction means for calculating the difference between the outputs of said third and fourth memories; and
computing means for obtaining a phase on the basis of output values of said first and second subtraction means.

* * * * *